US009957320B2

(12) United States Patent
Gozzard et al.

(10) Patent No.: US 9,957,320 B2
(45) Date of Patent: May 1, 2018

(54) ISOLATED DNA SEQUENCES ENCODING, AND METHODS FOR MAKING, ANTIBODY MOLECULES HAVING BINDING SPECIFICITY FOR HUMAN IL-13

(71) Applicant: UCB BIOPHARMA SPRL, Brussels (BE)

(72) Inventors: Neil Gozzard, Slough (GB); Alastair David Griffiths Lawson, Slough (GB); Daniel John Lightwood, Slough (GB); Roger Thomas Palframan, Slough (GB); Bryan John Smith, Slough (GB); Kerry Louise Tyson, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days. days.

(21) Appl. No.: 15/180,916

(22) Filed: Jun. 13, 2016

(65) Prior Publication Data
US 2016/0289323 A1 Oct. 6, 2016

Related U.S. Application Data

(62) Division of application No. 14/186,074, filed on Feb. 21, 2014, now Pat. No. 9,394,361, which is a division of application No. 12/720,804, filed on Mar. 10, 2010, now Pat. No. 8,691,233.

(30) Foreign Application Priority Data

Mar. 11, 2009 (GB) .................... 0904214.4

(51) Int. Cl.
*C07K 16/24* (2006.01)
*A61K 39/395* (2006.01)
*A61K 9/00* (2006.01)
*A61K 39/00* (2006.01)

(52) U.S. Cl.
CPC .......... *C07K 16/244* (2013.01); *A61K 9/0078* (2013.01); *A61K 39/3955* (2013.01); *A61K 39/395* (2013.01); *A61K 2039/505* (2013.01); *A61K 2039/544* (2013.01); *C07K 2317/24* (2013.01); *C07K 2317/33* (2013.01); *C07K 2317/51* (2013.01); *C07K 2317/515* (2013.01); *C07K 2317/55* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| 4,741,900 | A | 5/1988 | Alvarez et al. |
| 5,219,996 | A | 6/1993 | Bodmer et al. |
| 5,223,409 | A | 6/1993 | Ladner et al. |
| 5,403,484 | A | 4/1995 | Ladner et al. |
| 5,427,908 | A | 6/1995 | Dower et al. |
| 5,516,637 | A | 5/1996 | Huang et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,596,072 | A | 1/1997 | Culpepper et al. |
| 5,625,126 | A | 4/1997 | Lonberg et al. |
| 5,633,425 | A | 5/1997 | Lonberg et al. |
| 5,652,123 | A | 7/1997 | Caput et al. |
| 5,658,727 | A | 8/1997 | Barbas et al. |
| 5,661,016 | A | 8/1997 | Lonberg et al. |
| 5,667,425 | A | 9/1997 | Pineau et al. |
| 5,698,426 | A | 12/1997 | Huse |
| 5,733,743 | A | 3/1998 | Johnson et al. |
| 5,750,753 | A | 5/1998 | Kimae et al. |
| 5,770,429 | A | 6/1998 | Lonberg et al. |
| 5,780,225 | A | 7/1998 | Wigler et al. |
| 5,821,047 | A | 10/1998 | Garrard et al. |
| 5,969,108 | A | 10/1999 | McCafferty et al. |
| 7,078,494 | B1 | 7/2006 | Collins et al. |
| 2004/0115194 | A1 | 6/2004 | Wang |
| 2005/0271660 | A1 | 12/2005 | Wang |
| 2006/0063228 | A1 | 3/2006 | Kasaian et al. |
| 2006/0140948 | A1 | 6/2006 | Foltz et al. |
| 2008/0075720 | A1 | 3/2008 | Holers et al. |

FOREIGN PATENT DOCUMENTS

| EP | 0392745 A2 | 10/1990 |
| EP | 0438474 A1 | 7/1991 |
| EP | 0463151 A1 | 1/1992 |
| EP | 0546073 A1 | 6/1993 |
| EP | 0948544 A1 | 10/1999 |
| EP | 1090037 A1 | 4/2001 |

(Continued)

OTHER PUBLICATIONS

Adair et al., Therapeutic antibodies. *Drug Design Rev. Online*, 2(3): 209-17 (2005).
Akaiwa et al., Localization of human interleukin 13 receptor in non-haematopoietic cells. *Cytokine*, 13(2): 75-84 (2001).
Altschul et al., Basic local alignment search tool. *J. Mol. Biol.* 215(3): 403-10 (1990).
Altschul et al., Gapped BLAST and PSI-BLAST: a new generation of protein database search programs. *Nucl. Acids Res.* 25: 3389-402 (1997).
Aman et al., cDNA cloning and characterization of the human interleukin 13 receptor a chain. *J. Biol. Chem.* 271(46): 29265-70 (1996).

(Continued)

*Primary Examiner* — Bridget E Bunner
*Assistant Examiner* — Fozia Hamud
(74) *Attorney, Agent, or Firm* — Marshall, Gerstein & Borun LLP

(57) ABSTRACT

The invention relates to antibody molecules having specificity for antigenic determinants of human IL-13, therapeutic uses of the antibody molecules and methods for producing antibody molecules.

8 Claims, 16 Drawing Sheets

(56) References Cited

FOREIGN PATENT DOCUMENTS

| | | |
|---|---|---|
| GB | 2403952 A | 1/2005 |
| WO | WO-1986/001533 A1 | 3/1986 |
| WO | WO-1989/000195 A1 | 1/1989 |
| WO | WO-1989/001476 A1 | 2/1989 |
| WO | WO-1990/002809 A1 | 3/1990 |
| WO | WO-1991/009967 A1 | 7/1991 |
| WO | WO-1991/010737 A1 | 7/1991 |
| WO | WO-1992/001047 A1 | 1/1992 |
| WO | WO-1992/002551 A1 | 2/1992 |
| WO | WO-1992/018619 A1 | 10/1992 |
| WO | WO-1992/022583 A2 | 12/1992 |
| WO | WO-1993/006231 A1 | 4/1993 |
| WO | WO-1993/011236 A1 | 6/1993 |
| WO | WO-1995/015982 A2 | 6/1995 |
| WO | WO-1995/020401 A1 | 8/1995 |
| WO | WO-1998/020734 A1 | 5/1998 |
| WO | WO-1998/025971 A1 | 6/1998 |
| WO | WO-2000/064944 A1 | 11/2000 |
| WO | WO-2003/031581 A2 | 4/2003 |
| WO | WO-2003/086457 A2 | 10/2003 |
| WO | WO-2004/051268 A1 | 6/2004 |
| WO | WO-2004/072116 A2 | 8/2004 |
| WO | WO-2004/106377 A1 | 12/2004 |
| WO | WO-2005/003169 A2 | 1/2005 |
| WO | WO-2005/003170 A2 | 1/2005 |
| WO | WO-2005/003171 A2 | 1/2005 |
| WO | WO-2005/007699 A2 | 1/2005 |
| WO | WO-2005/062967 A2 | 7/2005 |
| WO | WO-2005/079755 A2 | 9/2005 |
| WO | WO-2005/081873 A2 | 9/2005 |
| WO | WO-2005/091853 A2 | 10/2005 |
| WO | WO-2005/091856 A2 | 10/2005 |
| WO | WO-2005/113605 A1 | 12/2005 |
| WO | WO-2005/117984 A2 | 12/2005 |
| WO | WO-2005/123126 A2 | 12/2005 |
| WO | WO-2006/003407 A2 | 1/2006 |
| WO | WO-2006/055638 A2 | 5/2006 |
| WO | WO-2006/063228 A2 | 6/2006 |
| WO | WO-2006/085938 A2 | 8/2006 |
| WO | WO-2006/124451 A2 | 11/2006 |
| WO | WO-2007/003898 A1 | 1/2007 |
| WO | WO-2007/036745 A2 | 4/2007 |
| WO | WO-2007/045477 A2 | 4/2007 |
| WO | WO-2007/080174 A2 | 7/2007 |
| WO | WO-2007/082068 A2 | 7/2007 |
| WO | WO-2008/073463 A2 | 6/2008 |
| WO | WO-2008/086043 A2 | 7/2008 |
| WO | WO-2008/086395 A2 | 7/2008 |
| WO | WO-2008/127271 A2 | 10/2008 |
| WO | WO-2009/040562 A1 | 4/2009 |
| WO | WO-2009/068649 A2 | 6/2009 |
| WO | WO-2010/021874 A2 | 2/2010 |

OTHER PUBLICATIONS

Ames et al., Conversion of murine Fabs isolated from a combinatorial phage display library to full length immunoglobulins. *J. Immunol. Meth.* 184(2): 177-86 (1995).

Angal et al., A single amino acid substitution abolishes the heterogeneity of chimeric mouse/human (IgG4) antibody. *Molec. Immunol.* 30(1): 105-8 (1993).

Arima et al., Upregulation of IL-3 concentration in vivo by the IL13 variant associated with bronchial asthma. *J Allergy Clin. Immunol.* 109(6): 980-7 (2002).

Babcook et al., A novel strategy for generating monoclonal antibodies from single, isolated lymphocytes producing antibodies of defined specificities. *Proc. Natl. Acad. Sci. USA*, 93(15): 7843-8 (1996).

Bebbington et al., High-level expression of a recombinant antibody from myeloma cells using a glutatime synthetase gene as an amplifiable selectable marker. *Biotechnol.* 10(2): 169-75 (1992).

Berry et al., In vitro and in vivo characterisation of anti-murine IL-13 antibodies recognizing distinct functional epitopes. *Internatl. Immunopharmacol.* 9: 201-6 (2008).

Berry et al., Sputum and bronchial submucosal IL-13 expression in asthma and eosinophilic bronchitis. *J. Allergy Clin. Immunol.* 114(5): 1106-9 (2004).

Brinkman et al., Phage display of disulfide-stabilized FV fragments. *J. Immunol. Meth.* 182(1): 11-50 (1995).

Brorson et al., Mutational analysis of Avidit and fine specificity of anti-Levan antibodies. *J. Immunol.* 163: 6694-701 (1999).

Brummell et al. Biochemistry, Probing the Combining Site of an Anti-Carbohydrate Antibody by Saturation-Mutagenesis: Role of the Heavy-Chain CDR3 Residues, 32: 1180-7 (1993).

Burks et al., In vitro scanning saturation mutagenesis of an antibody binding pocket. *Proc. Natl. Acad. Sci. USA*, 94: 412-7 (1997).

Burton et al., Human antibodies from combinatorial libraries. *Adv. Immunol.* 57: 191-280 (1994).

Casset et al., A peptide mimetic of an anti-CD4 monoclonal antibody by rational design. *Biochem. Biophys. Res. Commun.* 307: 198-205 (2003).

CDP-7766 flyer, A potent inhaled anti-IL13 Fab fragment for the treatment of severe asthma, UCB New Medicines, Slough, United Kingdom, post—May 19, 2009.

Chapman, PEGylated antibodies and antibody fragments for improved therapy: a review. *Adv. Drug Deliv. Rev.* 54: 531-45 (2002).

Chen et al., Functional effect of the R110Q1L13 genetic variant alone and in combination with IL4RA genetic variants. *J. Allergy Clin. Immunol.* 114(3): 553-60 (2004).

Chothia et al., Canonical structures for the hypervariable regions of immunoglobulins. *J. Mol. Biol.* 196: 901-17 (1987).

Cole et al., The EBV-hybridoma technique and its application to human lung cancer. Monoclonal Antibodies and Cancer Therapy, pp. 77-96, Alan R. Liss, Inc. (1985).

Colman, Effects of amino acid sequence changes on antibody-antigen interactions. *Res. Immunol.* 145: 33-6 (1994).

Crameri et al., DNA shuffling of a family of genes from diverse species accelerates directed evolution. *Nature*, 391: 288-91 (1998).

Crystal et al., Transfer of genes to humans: Early lessons and obstacles to success. *Science*, 270: 404-10 (1995).

De Waal et al., Effects of IL-13 on phenotype, cytokine production, and cytotoxic function of human monocytes. *J. Immunol.* 151: 6370-80 (1993).

Doherty, Modulation of murine macrophage function by IL-13. *J. Immunol.* 151(12): 7151-60 (1993).

Donaldson et al., The murine IL-13 receptor a2: Molecular cloning, characterization, and comparison with murine IL-13 receptor α11. *J. Immunol.* 61: 2317-24 (1998).

Dubowchik et al., Receptor-mediated and enzyme dependent targeting of cytotoxic anticancer drugs. *Pharmacol. Therapeut.* 83(2): 67-123 (1999).

Ericsson et al., Thermofluor-based throughput stability optimization of proteins for structural studies. *Anal. Biochem.* 357(2): 289-98 (2006).

Fichtner-Feigi et al., IL-13 signaling through the IL-13alpha2 receptor is involved in induction of TGF-beta production and fibrosis. *Nat. Med.* 12(1): 99-106 (2006).

Gish et al., Identification of protein coding regions by database similarity search. *Nature Genet.* 3: 266-72 (1993).

Graber et al., The distribution of IL-13 receptor alpha! expression on B cells, T cells and monocytes and its regulation by IL-13 and IL-4. *Eur. J. Immunol.* 28: 4286-98 (1998).

Grunig et al., Requirement for IL-13 independently of IL-4 in experimental asthma. *Science*, 282(5397): 2261-3 (1998).

Harris et al., Processing of C-terminal lysine and arginine residues of proteins isolated from mammalian cell culture. *J. Chromat.* 705(1): 129-34 (1995).

Heinzmann et al., Association study of the IL13 variant Arg110Gln in atopic diseases and juvenile idiopathic arthritis. *J. Allergy Clin. Immunol.* 112: 735-9 (2003).

Heinzmann et al., Genetic variants of IL-13 signalling and human asthma and atopy. *Hum. Molec. Genet.* 9(4): 549-59 (2000).

(56) References Cited

OTHER PUBLICATIONS

Hellstrom et al., Antibodies for Drug Delivery, Controlled Drug Delivery, 2nd Ed., Robinson et al., eds., pp. 323-653, Marcel Dekker, Inc. (1987).
Hieter et al., Evolution of human immunoglobulin K J region genes. *J. Biol. Chem.* 257(3): 1516-22 (1982).
Hilton et al., Cloning and characterization of a binding subunit of the interleukin 13 receptor that is also a component of the interleukin 4 receptor. *Proc Natl Acad Sci USA*, 93: 497-501 (1996).
Hoerauf, A., et al., The variant Arg110Gln of human IL-13 is associated with an immunologically hyper-reactive form of onchocerciasis (sowda). *Microbes Infect.* 4: 37-42 (2002).
Holliger et al., Engineered antibody fragments and the rise of single domains. *Nat. Biotechnol.* 23(9): 1126-36 (2005).
Huang et al., IL-13 expression at the sites of allergen challenge in patients with asthma. *J. Immunol.* 155(5): 2688-94 (1995).
International Search Report of PCT International Application No. PCT/GB2010/000432, dated Jul. 22, 2010.
Jang et al., The structural basis for DNA binding by an anti-DNA autoantibody. *Molec. Immunol.* 35: 1207-17 (1998).
Juengst et al., What next for human gene therapy? *Brit. Med. J.* 326: 1410-11 (2003).
Kasaian et al., Interleukin-13 neutralization by two distinct receptor blocking mechanisms reduces imunoglobulin E responses and lung inflammation in cynomolgus monkeys. *J. Pharmacol. Exp. Therapeut.* 325(3): 882-92 (2008).
Kashmiri et al., SDR grafting—a new approach to antibody humanization. *Methods*, 36: 25-34 (2005).
Kettleborough et al., Isolation of tumor cell-specific single-chain Fv from immunized mice using phage-antibody libraries and the reconstruction of whole antibodies from these antibody fragments. *Eur. J. Immunol.* 24(4): 952-8 (1994).
Kibe et al., Differential regulation by glucocorticoid of interleukin-13-induced eosinophilia, hyperresponsiveness, and goblet cell hyperplasia in mouse airways. *Am. J. Respir. Crit. Care Med.* 167: 50-6 (2003).
Kobayashi et al., Tryptophan H33 plays an important role in pyrimidine (6-4) pyrimidine photoproduct binding by a sigh-affinity antibody. *Protein Engin.* 12: 879-84 (1999).
Kohler et al., Continuous cultures of fused cells secreting antibody of predefined specificity. *Nature*, 256: 495-7 (1975).
Kozbor et al., The production of monoclonal antibodies from human lymphocytes. *Immunol. Today*, 4(3): 72-9 (1983).
Kuperman et al., Direct effects of interleukin-13 on epithelial cells cause airway hyperreactivity and mucus overproduction in asthma. *Nat. Med.* 8(8): 885-9 (2002).
Lanone et al., Overlapping and enzyme-specific contributions of matrix metalloproteinases-9 and -12 in IL-13-induced inflammation and remodeling. *J. Clin. Invest.* 110(4): 463-74 (2002).
Low et al., Mimicking somatic hypermutation: affinity maturation of antibodies displayed on bacteriophage using a bacterial mutator strain. J. Mol. Biol. 260: 359-68 (1996).
Madden et al., Network BLAST server applications. *Meth. Enzymol.* 266: 131-41 (1996).
Malefyt et al., Effects of IL-13 on phenotype, cytokine production, and cytotoxic function of human nonocytes. Comparison with IL-4 and modulation by IFN-gamma or IL-10. *J. Immunol.* 151(11): 6370-81 (1993).
Marks et al., By-passing immunization human: Building high affinity human antibodies by chain shuffling. *Bio/Technology*, 10: 779-83 (1992).
Murata et al., Two different IL-13 receptor chains are expressed in normal human skin fibroblasts, and IL-4 and IL-13 mediate signal transduction through a common pathway, Int. Immunol., vol. 10, No. 8, pp. 1103-1110,1998.
Patten et al., Applications of DA shuffling to pharmaceuticals and vaccines. *Curr. Opin. Biotechnol.* 8(6): 724-33 (1997).
Paul et al., Chapter 8: Immunogenicity and Antigen Structure, Fundamental Immunology, 3rd Edition, pp. 292-295 (1993).
Persic et al., An integrated vector system for the eukaryotic expression of antibodies or their fragments after selection from phage display libraries. *Gene*, 187(1): 9-18 (1997).
Punnonen et al., Interleukin 13 induces interleukin 4-independent IgG4 and IgE synthesis and CD23 expression by human B cells. *Proc. Natl. Acad. Sci. USA*, 90: 3730-4 (1993).
Ravetch et al., Structure of the human immunoglobulin μ locus: Characterization of embryonic and rearranged J and D genes. *Cell*, 27: 583-91 (1981).
Riechmann et al., Reshaping human antibodies for therapy. *Nature*, 332: 323-4 (1998).
Rubanyi et al., The future of human gene therapy. *Molec. Aspects Med.* 22: 113-42 (2001).
Seia, Cytokin IL-13: A central intermediary in the asthma development mechanism. *Pathol. Chem. Inst.* 137: 317-9 (1999).
Takeda et al., Impaired IL-13-mediated functions of macrophages in STAT6-deficient mice. *J. Immunol.* 157: 3220-2 (1996).
Taube et al., The role of IL-13 in established allergic airway disease. *J. Immunol.* 169: 6482-9 (2002).
Thompson et al., Affinity maturation of a high-affinity human monoclonal antibody against the third hypervariable loop of human immunodeficiency virus: use of phage display to improve affinity and broaden strain reactivity. *J. Mol. Biol.* 256: 77-88 (1996).
Thorpe et al., The preparation ad cytotoxic properties of antibody-toxin conjugates. *Immunol Rev.* 62: 119-58 (1982).
Vargaftig et al., Leukotrienes mediate murine bronchopulmonary hyperreactivity, inflammation, and part of mucosal metaplasia and tissue injury induced by recombinant murine interleukin-13. *Am. J. Respir. Cell Mol. Biol.* 28: 410-9 (2003).
Vargaftig et al., Leukotrienes, IL-13, and chemokines cooperate to induce BHR and mucus in allergic mouse lungs. *Am. J. Physiol. Lung Cell Mol. Physiol.* 284: L260-9 (2003).
Vaughan et al., Human antibodies by design. *Nat. Biotechnol.* 16(6): 535-9 (1998).
Vercelli, Genetics of IL-13 and functional relevance of IL-13 variants. *Curr. Opin. Allergy Clin. Immunol.* 2: 389-93 (2002).
Verma et al., Antibody engineering: comparison of bacterial, yeast, insect and mammalian expression systems. *J. Immunol. Meth.* 216(1-2): 165-81 (1998).
Vladich et al., IL-13 R130Q, a common variant associated with allergy and asthma, enhances effector mechanisms essential for human allergic inflammation. *J. Clin. Invest.* 115(3): 747-54 (2005).
Vugmeyster et al., Preclinical pharmacokinetics, interspecies scaling, and tissue distribution of humanized monoclonal anti-IL-13 antibodies with different IL-13 neutralization mechanisms. *Internatl. Immunopharmacol.* 8: 477-83 (2008).
Wang et al., The insulin receptor substrate-I-related 4PS substrate but not the interleukin-2R gamma chain is involved in interleukin-13-mediated signal transduction. *Blood*, 86: 4218-27 (1995).
Wills-Karp et al., Interleukin-13 in asthma. *Curr. Opin. Pulm. Med.* 9(1): 21-7 (2003).
Wills-Karp et al., Interleukin-13: Central mediator of allergic asthma. *Science*, 282(5397): 2258-61 (1998).
Wills-Karp, Inerleukin-13 in asthma pathogenesis. *Immunol. Rev.* 202: 175-90 (2004).
Wills-Karp, The gene encoding interleukin-13: A susceptibility locus for asthma and related traits. *Respir. Res.* 1(1): 19-23 (2000).
Yang et al., CDR walking mutagenesis for the affinity maturation of a potent human anti-HTV-1 antibody into the picomolar range. *J. Mol. Biol.* 254: 392-403 (1995).
Yang et al., Therapeutic dosing with anti-interleukin-13 monoclonal antibody inhibits asthma progression in mice. *J. Pharmacol. Exp. Ther.* 313(1): 8-15 (2005).
Zhang et al., PowerBLAST: a new network BLAST application for interactive or automated sequence analysis and annotation. *Genome Res.* 7(6): 649-56 (1997).
Zhu et al., Airway inflammation and remodeling in asthma-lessons from interleukin 11 and interleukin 13 transgenic mice. *Am. J. Respir. Crit. Care Med.* 164: S67-70 (2001).
Zhu et al., Pulmonary expression of interleukin-13 causes inflammation, mucous hypersecretion, subepithelial fibrosis, physiologic abnormalities, and eotaxin production. *J. Clin. Invest.* 103: 779-88 (1999).

(56) References Cited

OTHER PUBLICATIONS

Zubler et al., Mutant EL-4 thymoma cells polyclonally activate murine and human B cells via direct cell interaction. *J. Immunol.* 134(6): 3662-8 (1985).

Zurawski et al., Interleukin 13, an interleukin 4-like cytokine tht acts on monocytes and B cells, but not on T cells. *Immunol. Today*, 15(1): 19-26 (1994).

FIGURE 1

SEQ ID No: 1  CDR H1
GFSLTNYHVQ

SEQ ID No: 2  CDR H2
VMWSDGDTSFNSVLKS

SEQ ID No: 3  CDR H3
DGTIAAMDYFDY

SEQ ID No: 4  CDR L1
LASEDISNYLA

SEQ ID No: 5  CDR L2
HTSRLQD

SEQ ID No: 6  CDR L3
QQGYRFPLT

SEQ ID No: 7  Rat Ab VL region CDRs in bold
DIQMTQSPHS LSASLGETVS IECLASEDIS NYLAWYQQKP GKSPQLLIYH
TSRLQDGVPS RFSGSGSGTQ FSLKISNMQP EDEGVYYCQQ GYRFPLTFGS
GTKLELK

SEQ ID No: 8  Rat Ab VL region
gacatccaga tgacacagtc tccacattcc ctgtctgcat ctctgggaga
aactgtctcc atcgaatgtc tagcaagtga ggacatttcc aattatttag
cgtggtatca gcagaagcca ggaaaatctc ctcagctctt gatctatcat
acaagtaggt tgcaagatgg ggtcccatca cggttcagtg gcagtggatc
tggcacacag ttttctctca agatcagtaa catgcaacct gaagatgaag
gggtctatta ctgtcaacag ggttacaggt ttccgctcac gttcggttct
gggaccaagc tggaattgaa a

SEQ ID No: 9  Rat Ab VL region with signal sequence underlined
<u>MGVPTQLLGL LLLWITDAIC</u> DIQMTQSPHS LSASLGETVS IECLASEDIS
NYLAWYQQKP GKSPQLLIYH TSRLQDGVPS RFSGSGSGTQ FSLKISNMQP
EDEGVYYCQQ GYRFPLTFGS GTKLELK

FIGURE 2

SEQ ID No: 10    Rat Ab VL region with signal sequence underlined

<u>atgggtgtcc ccactcagct cttggggttg ttgttactgt ggattacaga</u>
<u>tgccatatgt</u> gacatccaga tgacacagtc tccacattcc ctgtctgcat
ctctgggaga aactgtctcc atcgaatgtc tagcaagtga ggacatttcc
aattatttag cgtggtatca gcagaagcca ggaaaatctc ctcagctctt
gatctatcat acaagtaggt tgcaagatgg ggtcccatca cggttcagtg
gcagtggatc tggcacacag ttttctctca agatcagtaa catgcaacct
gaagatgaag gggtctatta ctgtcaacag gttacaggt ttccgctcac
gttcggttct gggaccaagc tggaattgaa a

SEQ ID No: 11    Rat Ab light chain (V + constant)

DIQMTQSPHS LSASLGETVS IECLASEDIS NYLAWYQQKP GKSPQLLIYH
TSRLQDGVPS RFSGSGSGTQ FSLKISNMQP EDEGVYYCQQ GYRFPLTFGS
GTKLELKRAD AAPTVSIFPP STEQLATGGA SVVCLMNNFY PRDISVKWKI
DGTERRDGVL DSVTDQDSKD STYSMSSTLS LTKADYESHN LYTCEVVHKT
SSSPVVKSFN RNEC

SEQ ID No: 12    Rat Ab light chain (V + constant)

gacatccaga tgacacagtc tccacattcc ctgtctgcat ctctgggaga
aactgtctcc atcgaatgtc tagcaagtga ggacatttcc aattatttag
cgtggtatca gcagaagcca ggaaaatctc ctcagctctt gatctatcat
acaagtaggt tgcaagatgg ggtcccatca cggttcagtg gcagtggatc
tggcacacag ttttctctca agatcagtaa catgcaacct gaagatgaag
gggtctatta ctgtcaacag gttacaggt ttccgctcac gttcggttct
gggaccaagc tggaattgaa acgggctgat gctgcaccaa ctgtatctat
cttcccacca tccacggaac agttagcaac tggaggtgcc tcagtcgtgt
gcctcatgaa caacttctat cccagagaca tcagtgtcaa gtggaagatt
gatggcactg aacgacgaga tggtgtcctg acagtgtta ctgatcagga
cagcaaagac agcacgtaca gcatgagcag caccctctcg ttgaccaagg
ctgactatga aagtcataac ctctatacct gtgaggttgt tcataagaca
tcatcctcac ccgtcgtcaa gagcttcaac aggaatgagt gt

SEQ ID No: 13    Rat Ab light chain with signal sequence underlined

<u>MGVPTQLLGL LLLWITDAIC</u> DIQMTQSPHS LSASLGETVS IECLASEDIS
NYLAWYQQKP GKSPQLLIYH TSRLQDGVPS RFSGSGSGTQ FSLKISNMQP
EDEGVYYCQQ GYRFPLTFGS GTKLELKRAD AAPTVSIFPP STEQLATGGA
SVVCLMNNFY PRDISVKWKI DGTERRDGVL DSVTDQDSKD STYSMSSTLS
LTKADYESHN LYTCEVVHKT SSSPVVKSFN RNEC

FIGURE 3

SEQ ID No: 14      Rat Ab light chain with signal sequence underlined

<u>atgggtgtcc ccactcagct cttggggttg ttgttactgt ggattacaga</u>
<u>tgccatatgt</u> gacatccaga tgacacagtc tccacattcc ctgtctgcat
ctctgggaga aactgtctcc atcgaatgtc tagcaagtga ggacatttcc
aattatttag cgtggtatca gcagaagcca ggaaaatctc ctcagctctt
gatctatcat acaagtaggt tgcaagatgg ggtcccatca cggttcagtg
gcagtggatc tggcacacag ttttctctca agatcagtaa catgcaacct
gaagatgaag gggtctatta ctgtcaacag gttacaggt ttccgctcac
gttcggttct gggaccaagc tggaattgaa acgggctgat gctgcaccaa
ctgtatctat cttcccacca tccacggaac agttagcaac tggaggtgcc
tcagtcgtgt gcctcatgaa caacttctat cccagagaca tcagtgtcaa
gtggaagatt gatggcactg aacgacgaga tggtgtcctg gacagtgtta
ctgatcagga cagcaaagac agcacgtaca gcatgagcag caccctctcg
ttgaccaagg ctgactatga aagtcataac ctctatacct gtgaggttgt
tcataagaca tcatcctcac ccgtcgtcaa gagcttcaac aggaatgagt
gt

SEQ ID No: 15      Rat Ab VH region

QVQLKESPG LVQPSQTLSL TCTVSGFSLT NYHVQWVRQP PGKGLEWMGV
MWSDGDTSFN SVLKSRLSIS RDTSKSQVFL KMSSLQTEDT ATYYCARDGT
IAAMDYFDYW GQGVMVTVS

SEQ ID No: 16      Rat Ab VH region caggtgcagc tgaaggagtc aggacctggc ctggtgcagc cctcacagac
cctgtctctc acctgcactg tctctggtt ctcattaacc aactatcatg
tgcagtgggt tcggcagcct ccaggaaaag gtctggagtg gatgggagta
atgtggagtg atggagacac atcatttaat tcagttctca aatctcgact
gagcatcagc agggacacct ccaagagcca agttttctta aaaatgagca
gtctgcaaac tgaagacaca gccacttact actgtgccag agatggaact
atagcagcta tggactactt tgattattgg ggccaaggag tcatggtcac
cgtctcg

SEQ ID No: 17      Rat Ab VH region with signal sequence underlined

<u>MAVLVLLLCL MTFPSCVLSQ</u> VQLKESGPGL VQPSQTLSLT CTVSGFSLTN
YHVQWVRQPP GKGLEWMGVM WSDGDTSFNS VLKSRLSISR DTSKSQVFLK
MSSLQTEDTA TYYCARDGTI AAMDYFDYWG QGVMVTVS

FIGURE 4

SEQ ID No: 18      Rat Ab VH region with signal sequence underlined

<u>atggctgtcc tggtgctgtt gctctgcctg atgacatttc caagctgtgt</u>
<u>cctgtcccag</u> gtgcagctga aggagtcagg acctggcctg gtgcagccct
cacagaccct gtctctcacc tgcactgtct ctgggttctc attaaccaac
tatcatgtgc agtgggttcg gcagcctcca ggaaaaggtc tggagtggat
gggagtaatg tggagtgatg gagacacatc atttaattca gttctcaaat
ctcgactgag catcagcagg gacacctcca agagccaagt tttcttaaaa
atgagcagtc tgcaaactga agacacagcc acttactact gtgccagaga
tggaactata gcagctatgg actactttga ttattggggc caaggagtca
tggtcaccgt ctcg

SEQ ID No: 19      Rat Ab heavy chain (V + constant)

QVQLKESGPG LVQPSQTLSL TCTVSGFSLT NYHVQWVRQP PGKGLEWMGV
MWSDGDTSFN SVLKSRLSIS RDTSKSQVFL KMSSLQTEDT ATYYCARDGT
IAAMDYFDYW GQGVMVTVSS AETTAPSVYP LAPGTALKSN SMVTLGCLVK
GYFPEPVTVT WNSGALSSGV HTFPAVLQSG LYTLTSSVTV PSSTWPSQTV
TCNVAHPASS TKVDKKIVPR NCGGDCKPCI CTGSEVSSVF IFPPKPKDVL
TITLTPKVTC VVVDISQDDP EVHFSWFVDD VEVHTAQTRP PEEQFNSTFR
SVSELPILHQ DWLNGRTFRC KVTSAAFPSP IEKTISKPEG RTQVPHVYTM
SPTKEEMTQN EVSITCMVKG FYPPDIYVEW QMNGQPQENY KNTPPTMDTD
GSYFLYSKLN VKKEKWQQGN TFTCSVLHEG LHNHHTEKSL SHSPGK

FIGURE 5

SEQ ID No: 20        Rat Ab heavy chain (V + constant)

caggtgcagc tgaaggagtc aggacctggc ctggtgcagc cctcacagac
cctgtctctc acctgcactg tctctggttt ctcattaacc aactatcatg
tgcagtgggt tcggcagcct ccaggaaaag gtctggagtg gatgggagta
atgtggagtg atggagacac atcatttaat tcagttctca aatctcgact
gagcatcagc agggacacct ccaagagcca agttttctta aaaatgagca
gtctgcaaac tgaagacaca gccacttact actgtgccag agatggaact
atagcagcta tggactactt tgattattgg ggccaaggag tcatggtcac
cgtctcgtca gctgaaacaa cagcccatc tgtctatcca ctggctcctg
gaactgctct caaaagtaac tccatggtga ccctgggatg cctggtcaag
ggctatttcc ctgagccagt caccgtgacc tggaactctg gagccctgtc
cagcggtgtg cacaccttcc cagctgtcct gcagtctggg ctctacactc
tcaccagctc agtgactgta ccctccagca cctggcccag ccagaccgtc
acctgcaacg tagcccaccc ggccagcagc accaaggtgg acaagaaaat
tgtgcccaga aactgtggag gtgattgcaa gccttgtata tgtacaggct
cagaagtatc atctgtcttc atcttccccc caaagcccaa agatgtgctc
accatcactc tgactcctaa ggtcacgtgt gttgtggtag acattagcca
ggacgatccc gaggtccatt tcagctggtt tgtagatgac gtggaagtcc
acacagctca gactcgacca ccagaggagc agttcaacag cactttccgc
tcagtcagtg aactccccat cctgcaccag gactggctca atggcaggac
gttcagatgc aaggtcacca gtgcagcttt cccatccccc atcgagaaaa
ccatctccaa acccgaaggc agaacacaag ttccgcatgt ataccatg
tcacctacca aggaagagat gacccagaat gaagtcagta tcacctgcat
ggtaaaaggc ttctatcccc cagacattta tgtggagtgg cagatgaacg
ggcagccaca ggaaaactac aagaacactc cacctacgat ggacacagat
gggagttact tcctctacag caagctcaat gtgaagaagg aaaaatggca
gcagggaaac acgttcacgt gttctgtgct gcatgaaggc ctgcacaacc
accatactga gaagagtctc tcccactctc cgggtaaa

SEQ ID No: 21        Rat Ab heavy chain with signal sequence underlined

<u>MAVLVLLLCL MTFPSCVLSQ</u> VQLKESGPGL VQPSQTLSLT CTVSGFSLTN
YHVQWVRQPP GKGLEWMGVM WSDGDTSFNS VLKSRLSISR DTSKSQVFLK
MSSLQTEDTA TYYCARDGTI AAMDYFDYWG QGVMVTVSSA ETTAPSVYPL
APGTALKSNS MVTLGCLVKG YFPEPVTVTW NSGALSSGVH TFPAVLQSGL
YTLTSSVTVP SSTWPSQTVT CNVAHPASST KVDKKIVPRN CGGDCKPCIC
TGSEVSSVFI FPPKPKDVLT ITLTPKVTCV VVDISQDDPE VHFSWFVDDV
EVHTAQTRPP EEQFNSTFRS VSELPILHQD WLNGRTFRCK VTSAAFPSPI
EKTISKPEGR TQVPHVYTMS PTKEEMTQNE VSITCMVKGF YPPDIYVEWQ
MNGQPQENYK NTPPTMDTDG SYFLYSKLNV KKEKWQQGNT FTCSVLHEGL
HNHHTEKSLS HSPGK

FIGURE 6

SEQ ID No: 22      Rat Ab heavy chain with signal sequence underlined

<u>atggctgtcc tggtgctgtt gctctgcctg atgacatttc caagctgtgt</u>
<u>cctgtcccag</u> gtgcagctga aggagtcagg acctggcctg gtgcagccct
cacagaccct gtctctcacc tgcactgtct ctgggttctc attaaccaac
tatcatgtgc agtgggttcg gcagcctcca ggaaaaggtc tggagtggat
gggagtaatg tggagtgatg gagacacatc atttaattca gttctcaaat
ctcgactgag catcagcagg gacacctcca agagccaagt tttcttaaaa
atgagcagtc tgcaaactga agacacagcc acttactact gtgccagaga
tggaactata gcagctatgg actactttga ttattggggc caaggagtca
tggtcaccgt ctcgtcagct gaaacaacag ccccatctgt ctatccactg
gctcctggaa ctgctctcaa aagtaactcc atggtgaccc tgggatgcct
ggtcaaggc tatttccctg agccagtcac cgtgacctgg aactctggag
ccctgtccag cggtgtgcac accttccag ctgtcctgca gtctgggctc
tacactctca ccagctcagt gactgtaccc tccagcacct ggcccagcca
gaccgtcacc tgcaacgtag cccacccggc cagcagcacc aaggtggaca
agaaaattgt gcccagaaac tgtggaggtg attgcaagcc ttgtatatgt
acaggctcag aagtatcatc tgtcttcatc ttcccccaa agcccaaaga
tgtgctcacc atcactctga ctcctaaggt cacgtgtgtt gtggtagaca
ttagccagga cgatcccgag gtccatttca gctggtttgt agatgacgtg
gaagtccaca cagctcagac tcgaccacca gaggagcagt tcaacagcac
tttccgctca gtcagtgaac tccccatcct gcaccaggac tggctcaatg
gcaggacgtt cagatgcaag gtcaccagtg cagctttccc atcccccatc
gagaaaacca tctccaaacc cgaaggcaga acacaagttc cgcatgtata
caccatgtca cctaccaagg aagagatgac ccagaatgaa gtcagtatca
cctgcatggt aaaaggcttc tatcccccag acatttatgt ggagtggcag
atgaacgggc agccacagga aaactacaag aacactccac ctacgatgga
cacagatggg agttacttcc tctacagcaa gctcaatgtg aagaaggaaa
aatggcagca gggaaacacg ttcacgtgtt ctgtgctgca tgaaggcctg
cacaaccacc atactgagaa gagtctctcc cactctccgg gtaaa

FIGURE 7

SEQ ID No: 23    Ab652 VL
DIQMTQSPSS LSASVGDRVT ITCLASEDIS NYLAWYQQKP GKAPKLLIYH
TSRLQDGVPS RFSGSGSGTD FTLTISSLQP EDFATYYCQQ GYRFPLTFGG
GTKVEIK

SEQ ID No: 24    Ab652 VL
gatatccaga tgacccagag tccaagcagt ctctccgcca gcgtaggcga
tcgtgtgact attacctgtc tggctagcga ggacatctcc aactacctgg
cgtggtatca gcagaaaccg ggtaaagcgc cgaaactgct gatctatcac
acttcccgtc tgcaggacgg tgttccgtct cgtttctctg gttccggttc
tggtacggac ttcaccctga ccatctcttc tctgcagcca gaagacttcg
cgacttacta ctgccagcag ggttaccgtt ttccgctgac cttcggtggt
ggtaccaaag ttgaaatcaa a

SEQ ID No: 25    Ab652 VL with signal sequence underlined
<u>MSVPTQVLGL</u> <u>LLLWLTDARC</u> DIQMTQSPSS LSASVGDRVT ITCLASEDIS
NYLAWYQQKP GKAPKLLIYH TSRLQDGVPS RFSGSGSGTD FTLTISSLQP
EDFATYYCQQ GYRFPLTFGG GTKVEIK

SEQ ID No: 26    Ab652 VL with signal sequence underlined
<u>atgtctgtcc</u> <u>ccacccaagt</u> <u>cctcggactc</u> <u>ctgctactct</u> <u>ggcttacaga</u>
<u>tgccagatgc</u> gatatccaga tgacccagag tccaagcagt ctctccgcca
gcgtaggcga tcgtgtgact attacctgtc tggctagcga ggacatctcc
aactacctgg cgtggtatca gcagaaaccg ggtaaagcgc cgaaactgct
gatctatcac acttcccgtc tgcaggacgg tgttccgtct cgtttctctg
gttccggttc tggtacggac ttcaccctga ccatctcttc tctgcagcca
gaagacttcg cgacttacta ctgccagcag ggttaccgtt ttccgctgac
cttcggtggt ggtaccaaag ttgaaatcaa a

SEQ ID No: 27    Ab652 light chain (V + constant)
DIQMTQSPSS LSASVGDRVT ITCLASEDIS NYLAWYQQKP GKAPKLLIYH
TSRLQDGVPS RFSGSGSGTD FTLTISSLQP EDFATYYCQQ GYRFPLTFGG
GTKVEIKRTV AAPSVFIFPP SDEQLKSGTA SVVCLLNNFY PREAKVQWKV
DNALQSGNSQ ESVTEQDSKD STYSLSSTLT LSKADYEKHK VYACEVTHQG
LSSPVTKSFN RGEC

FIGURE 8

SEQ ID No: 28      Ab652 light chain (V + constant)

```
gatatccaga tgacccagag tccaagcagt ctctccgcca gcgtaggcga
tcgtgtgact attacctgtc tggctagcga ggacatctcc aactacctgg
cgtggtatca gcagaaaccg ggtaaagcgc cgaaactgct gatctatcac
acttcccgtc tgcaggacgg tgttccgtct cgtttctctg gttccggttc
tggtacggac ttcaccctga ccatctcttc tctgcagcca gaagacttcg
cgacttacta ctgccagcag ggttaccgtt ttccgctgac cttcggtggt
ggtaccaaag ttgaaatcaa acgtacggta gcggcccat ctgtcttcat
cttcccgcca tctgatgagc agttgaaatc tggaactgcc tctgttgtgt
gcctgctgaa taacttctat cccagagagg ccaaagtaca gtggaaggtg
gataacgccc tccaatcggg taactccag gagagtgtca cagagcagga
cagcaaggac agcacctaca gcctcagcag caccctgacg ctgagcaaag
cagactacga gaaacacaaa gtctacgcct gcgaagtcac ccatcaggc
ctgagctcgc ccgtcacaaa gagcttcaac aggggagagt gt
```

SEQ ID No: 29      Ab652 light chain with signal sequence underlined

<u>MSVPTQVLGL</u> <u>LLLWLTDARC</u> DIQMTQSPSS LSASVGDRVT ITCLASEDIS
NYLAWYQQKP GKAPKLLIYH TSRLQDGVPS RFSGSGSGTD FTLTISSLQP
EDFATYYCQQ GYRFPLTFGG GTKVEIKRTV AAPSVFIFPP SDEQLKSGTA
SVVCLLNNFY PREAKVQWKV DNALQSGNSQ ESVTEQDSKD STYSLSSTLT
LSKADYEKHK VYACEVTHQG LSSPVTKSFN RGEC

SEQ ID No: 30      Ab652 light chain with signal sequence underlined

<u>atgtctgtcc</u> <u>ccacccaagt</u> <u>cctcggactc</u> <u>ctgctactct</u> <u>ggcttacaga</u>
<u>tgccagatgc</u> gatatccaga tgacccagag tccaagcagt ctctccgcca
gcgtaggcga tcgtgtgact attacctgtc tggctagcga ggacatctcc
aactacctgg cgtggtatca gcagaaaccg ggtaaagcgc cgaaactgct
gatctatcac acttcccgtc tgcaggacgg tgttccgtct cgtttctctg
gttccggttc tggtacggac ttcaccctga ccatctcttc tctgcagcca
gaagacttcg cgacttacta ctgccagcag ggttaccgtt ttccgctgac
cttcggtggt ggtaccaaag ttgaaatcaa acgtacggta gcggcccat
ctgtcttcat cttcccgcca tctgatgagc agttgaaatc tggaactgcc
tctgttgtgt gcctgctgaa taacttctat cccagagagg ccaaagtaca
gtggaaggtg gataacgccc tccaatcggg taactccag gagagtgtca
cagagcagga cagcaaggac agcacctaca gcctcagcag caccctgacg
ctgagcaaag cagactacga gaaacacaaa gtctacgcct gcgaagtcac
ccatcaggc ctgagctcgc ccgtcacaaa gagcttcaac aggggagagt
gt

FIGURE 9

SEQ ID No: 31    Ab652 VH
QVTLKESGPV LVKPTETLTL TCTVSGFSLT NYHVQWIRQP PGKALEWLGV
MWSDGDTSFN SVLKSRLTIS RDTSKSQVVL TMTNMDPVDT ATYYCARDGT
IAAMDYFDYW GQGTLVTVS

SEQ ID No: 32    Ab652 VH
caggtgaccc tgaaagaatc tggtccggtt ctggtgaaac caacggaaac
cctgactctg acgtgcaccg tttctggttt ctctctgacc aactaccacg
ttcagtggat cgtcagccg ccgggtaaag cgctggaatg gctgggtgtt
atgtggagcg acggtgacac cagcttcaac tctgtgctga atctcgcct
gaccatctcc cgtgatactt ccaaatccca ggttgtgctg accatgacga
acatggaccc ggtagatact gcaacctact actgtgcacg tgatggcact
atcgcggcta tggattactt cgactattgg ggtcagggta ccctggttac
cgtctcg

SEQ ID No: 33    Ab652 VH with signal sequence underlined
<u>MEWSWVFLFF LSVTTGVHSQ</u> VTLKESGPVL VKPTETLTLT CTVSGFSLTN
YHVQWIRQPP GKALEWLGVM WSDGDTSFNS VLKSRLTISR DTSKSQVVLT
MTNMDPVDTA TYYCARDGTI AAMDYFDYWG QGTLVTVS

SEQ ID No: 34    Ab652 VH with signal sequence underlined
<u>atggaatgga gctgggtctt tctcttcttc ctgtcagtaa ctacaggagt</u>
<u>ccattctcag</u> gtgaccctga agaatctgg tccggttctg gtgaaaccaa
cggaaaccct gactctgacg tgcaccgttt ctggtttctc tctgaccaac
taccacgttc agtggattcg tcagccgccg ggtaaagcgc tggaatggct
gggtgttatg tggagcgacg gtgacaccag cttcaactct gtgctgaaat
ctcgcctgac catctcccgt gatacttcca atcccaggt tgtgctgacc
atgacgaaca tggacccggt agatactgca acctactact gtgcacgtga
tggcactatc gcggctatgg attacttcga ctattggggt cagggtaccc
tggttaccgt ctcg

SEQ ID No: 35    Ab652 Fab heavy chain (V + constant)
QVTLKESGPV LVKPTETLTL TCTVSGFSLT NYHVQWIRQP PGKALEWLGV
MWSDGDTSFN SVLKSRLTIS RDTSKSQVVL TMTNMDPVDT ATYYCARDGT
IAAMDYFDYW GQGTLVTVSS ASTKGPSVFP LAPSSKSTSG GTAALGCLVK
DYFPEPVTVS WNSGALTSGV HTFPAVLQSS GLYSLSSVVT VPSSSLGTQT
YICNVNHKPS NTKVDKKVEP KSC

FIGURE 10

SEQ ID No: 36    Ab652 Fab heavy chain (V + constant)

```
caggtgaccc tgaaagaatc tggtccggtt ctggtgaaac caacggaaac
cctgactctg acgtgcaccg tttctggttt ctctctgacc aactaccacg
ttcagtggat tcgtcagccg ccgggtaaag cgctggaatg gctgggtgtt
atgtggagcg acggtgacac cagcttcaac tctgtgctga atctcgcct
gaccatctcc cgtgatactt ccaaatccca ggttgtgctg accatgacga
acatggaccc ggtagatact gcaacctact actgtgcacg tgatggcact
atcgcggcta tggattactt cgactattgg ggtcaggta ccctggttac
cgtctcgagc gcttctacaa agggcccatc ggtcttcccc ctggcaccct
cctccaagag cacctctggg ggcacagcgg ccctgggctg cctggtcaag
gactacttcc ccgaaccggt gacggtgtcg tggaactcag gcgccctgac
cagcggcgtg cacaccttcc cggctgtcct acagtcctca ggactctact
ccctcagcag cgtggtgacc gtgccctcca gcagcttggg cacccagacc
tacatctgca acgtgaatca caagcccagc aacaccaagg tggacaagaa
agttgagccc aaatcttgt
```

SEQ ID No: 37    Ab652 Fab heavy chain with signal sequence underlined

<u>MEWSWVFLFF</u> <u>LSVTTGVHSQ</u> VTLKESGPVL VKPTETLTLT CTVSGFSLTN
YHVQWIRQPP GKALEWLGVM WSDGDTSFNS VLKSRLTISR DTSKSQVVLT
MTNMDPVDTA TYYCARDGTI AAMDYFDYWG QGTLVTVSSA STKGPSVFPL
APSSKSTSGG TAALGCLVKD YFPEPVTVSW NSGALTSGVH TFPAVLQSSG
LYSLSSVVTV PSSSLGTQTY ICNVNHKPSN TKVDKKVEPK SC

SEQ ID No: 38    Ab652 Fab heavy chain with signal sequence underlined

<u>atggaatgga</u> <u>gctgggtctt</u> <u>tctcttcttc</u> <u>ctgtcagtaa</u> <u>ctacaggagt</u>
<u>ccattctcag</u> gtgaccctga aagaatctgg tccggttctg gtgaaaccaa
cggaaaccct gactctgacg tgcaccgttt ctggtttctc tctgaccaac
taccacgttc agtggattcg tcagccgccg ggtaaagcgc tggaatggct
gggtgttatg tggagcgacg gtgacaccag cttcaactct gtgctgaaat
ctcgcctgac catctcccgt gatacttcca atcccaggt tgtgctgacc
atgacgaaca tggacccggt agatactgca acctactact gtgcacgtga
tggcactatc gcggctatgg attacttcga ctattgggt cagggtaccc
tggttaccgt ctcgagcgct tctacaaagg gcccatcggt cttcccctg
gcaccctcct ccaagagcac ctctggggc acagcggccc tgggctgcct
ggtcaaggac tacttccccg aaccggtgac ggtgtcgtgg aactcaggcg
ccctgaccag cggcgtgcac accttccgg ctgtcctaca gtcctcagga
ctctactccc tcagcagcgt ggtgaccgtg ccctccagca gcttgggcac
ccagacctac atctgcaacg tgaatcacaa gcccagcaac accaaggtgg
acaagaaagt tgagcccaaa tcttgt
```

FIGURE 11

SEQ IN No: 39     Human VK1 2-1-(1) 02 JK4 acceptor framework
DIQMTQSPSS LSASVGDRVT ITCRASQSIS SYLNWYQQKP GKAPKLLIYA
ASSLQSGVPS RFSGSGSGTD FTLTISSLQP EDFATYYCQQ SYSTPLTFGG
GTKVEIK

SEQ ID No: 40     Human VK1 2-1-(1) O2 JK4 acceptor framework
gacatccaga tgacccagtc tccatcctcc ctgtctgcat ctgtaggaga
cagagtcacc atcacttgcc gggcaagtca gagcattagc agctatttaa
attggtatca gcagaaacca gggaagccc ctaagctcct gatctatgct
gcatccagtt tgcaaagtgg ggtcccatca aggttcagtg gcagtggatc
tgggacagat ttcactctca ccatcagcag tctgcaacct gaagattttg
caacttacta ctgtcaacag agttacagta cccctctcac tttcggcgga
gggaccaagg tggagatcaa ac

SEQ ID No: 41     Human VH2 3-1 2-26 JH4 acceptor framework
QVTLKESGPV LVKPTETLTL TCTVSGFSLS NARMGVSWIR QPPGKALEWL
AHIFSNDEKS YSTSLKSRLT ISKDTSKSQV VLTMTNMDPV DTATYYCARI
YFDYWGQGTL VTVS

SEQ ID No: 42     Human VH2 3-1 2-26 JH4 acceptor framework caggtcacct tgaaggagtc tggtcctgtg ctggtgaaac ccacagagac
cctcacgctg acctgcaccg tctctgggtt ctcactcagc aatgctagaa
tgggtgtgag ctggatccgt cagcccccag ggaaggccct ggagtggctt
gcacacattt tttcgaatga cgaaaaatcc tacagcacat ctctgaagag
caggctcacc atctccaagg acacctccaa aagccaggtg gtccttacca
tgaccaacat ggaccctgtg gacacagcca catattactg tgcacggata
tactttgact actggggcca aggaaccctg gtcaccgtct cc

FIGURE 12

Comparison of Light chains

```
              1   5   10  15  20  25  30  35  40  45  50  55  60  65  70  75  80  85  90  95  100 105
Light_Rat     DIQMTQSPHSLSASLGETVSIECLASEDISNYLAWYQQKPGKSPQLLIYHTSRLQDGVPSRFSGSGSGTQFSLKISNMQPEDEGVYYCQQGYRFPLTFGSGTKLELK
                                    | | |     || | |     | |   | |         |  | ||   ||      |      |   |  |
VK1 2-1-(1)O2 DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK Light Ab652   DIQMTQSPSSLSASVGDRVTITCLASEDISNYLAWYQQKPGKAPKLLIYHTSRLQDGVPSRFSGSGSGTDITLTISSLQPEDFATYYCQQGYRFPLTFGGGTKVEIK
```

Comparison of Heavy Chains

```
              1   5   10  15  20  25  30 ab 35  40  45  50  55  60  65  70  75  80 abc 85  90  95  100    105 110
Heavy Rat     QVQLKESGPGLVQPSQTLSLTCTVSGFSLTN   YHVQWVRQPPGKGLEWMGVMWSDGDTSFNSVLKSRLSISRDTSKSQVFLKMSSLQTEDTATYYCARDGTIAAMDYFDYWGQGVMVTVS
                                      |    | |      | |   || | |          || | || ||       | |    | | |                     |      ||
VH2 3-1 2-26  QVTLKESGPVLVKPTETLTLTCTVSGFSLSNARMGVSWIRQPPGKALEWLAHIFSNDEKSYSTSLKSRLTISKDTSKSQVVLTMTNYDPVTATYYCARI         YFDYWGQGTLVTVS
                                                                                |               |
Heavy Ab652   QVTLKESGPVLVKPTETLTLTCTVSGFSLTN   YHVQWIRQPPGKALEWLGVMWSDGDTSFNSVLKSRLTISRDTSKSQVVLTMTNYDPVTATYYCARDGTIAAMDYFDYWGQGTLVTVS
```

For Ab652 heavy chain, donor residues are shown in bold/italic and are highlighted: G49 and R71

ISOLATED DNA SEQUENCES ENCODING, AND METHODS FOR MAKING, ANTIBODY MOLECULES HAVING BINDING SPECIFICITY FOR HUMAN IL-13

CROSS REFERENCE TO RELATED APPLICATIONS AND INCORPORATION BY REFERENCE

This application is a divisional of U.S. patent application Ser. No. 14/186,074 (now U.S. Pat. No. 9,394,361), filed Feb. 21, 2014, which is a divisional of U.S. patent application Ser. No. 12/720,804 (now U.S. Pat. No. 8,691,233), filed Mar. 10, 2010, and claims priority under 35 U.S.C. § 119(a) to Great Britain Patent Application No. 0904214.4, filed Mar. 11, 2009, the entire contents of each of which are fully incorporated herein by reference.

This application containing, as a separate part of disclosure, a Sequence Listing in computer-readable form (filename: 50360A_SeqListing.txt; 50,673 bytes, created Jun. 10, 2016), which is incorporated by reference in its entirety.

The present invention relates to IL-13 antibodies and fragments thereof such as binding fragments thereof, compositions comprising the same, and specifically to their use in the prevention and/or treatment of various diseases including asthma, allergy, COPD, fibrosis, and/or cancer.

BACKGROUND OF THE INVENTION

IL-13 is a short-chain cytokine sharing 25% sequence identity with IL-4. It comprises approximately 132 amino acids, forming a secondary structure of four helices spanning residues 10-21 (helix A), 43-52 (helix B), 61-69 (helix C), and 92-110 (helix D), along with two β-strands spanning residues 33-36 and 87-90. The solution structure of IL-13 has been solved, revealing the predicted up-up-down-down four-helix-bundle conformation also observed with IL-4 (Eisenmesser 2001).

Human IL-13 is a 17-kDa glycoprotein cloned from activated T cells (Zurawski and de Vries 1994 Immunol Today 15 19-26), and is produced by activated T cells of the Th2 lineage, although Th0 and Th1 CD4+ T cells, CD8+ T cells, and several non-T cell populations such as mast cells also produce IL-13 (Zurawski and de Vries 1994 Immunol Today 13 19-26).

The function of IL-13 includes:
immunoglobulin isotype switching to IgE in human B cells (Punnonen, Aversa et al. 1993 Proc Natl Acad Sci USA 90 3730-4) and
suppressing inflammatory cytokine production in both humans and mice (de Waal Malefyt, Figdor et al. 1993 J Immunol 151 6370-81; Doherty, Kastelein et al. 1993 J Immunol 151 7151-60).

IL-13 binds to its cell surface receptors, IL-13 Ralpha1 and IL-13 Ralpha2. IL-13Ralpha1 interacts with IL-13 with a low affinity (KD ~10 nM), followed by recruitment of IL-4Ra to form the high affinity (KD ~0.4 nM) signaling heterodimeric receptor complex (Aman, Tayebi et al. 1996 J Biol Chem 271 29265-70; Hilton, Zhang et al. 1996 Proc Natl Acad Sci USA 93 497-501).

The IL-4R/IL-13Ralpha1 complex is expressed on many cell types such as B cells, monocyte/macrophages, dendritic cells, eosinophils, basophils, fibroblasts, endothelial cells, airway epithelial cells, and airway smooth muscle cells (Graber, Gretener et al. 1998 Eur J Immunol 28 4286-98; Murata, Husain et al. 1998 Int Immunol 10 1103-10; Akaiwa, Yu et al. 2001 Cytokine 13 75-84).

Ligation of the IL-13Ralpha1/IL-4R receptor complex results in activation of a variety of signal-transduction pathways including signal transducer and activator of transcription (ST AT6) and the insulin receptor substrate-2 (IRS-2) pathways (Wang, Michieli et al. 1995 Blood 864218-27; Takeda, Kamanaka et al. 1996 J Immunol 157 3220-2).

The IL-13Ralpha2 chain alone has a high affinity (KD ~0.25-0.4 nM) for IL-13, and functions as both a decoy receptor negatively regulating IL-13 binding (Donaldson, Whitters et al. 1998 J Immunol 161 2317-24), and a signaling receptor that induces TGF-b synthesis and fibrosis via AP-I pathway in macrophages and possibly other cell types (Fichtner-Feigl, Strober et al. 2006 Nat Med 12 99-106).

Several studies conducted in preclinical animal models for asthma indicate that IL-13 plays an important role in asthma. These data include resistance to asthma in the IL-13 knockout mice as well as inhibition of the asthma phenotype with IL-13 antagonists (soluble IL-13 receptors, anti-IL-13 mAbs, etc.) in various mouse models (Sela 1999 Harefuah 137 317-9; Wills-Karp and Chiaramonte 2003 Curr Opin Pulm Med 9 21-7; Wills-Karp 2004 Immunol Rev 202 175-90). Multiple studies have demonstrated that pharmacologic administration of recombinant IL-13 to the lungs of mice as well as guinea pigs induces airway mucus hyper-secretion, eosinophilia and AHR (Grunig, Warnock et al. 1998 Science 282 2261-3; Wills-Karp, Luyimbazi et al. 1998 Science 282 2258-61; Kibe, Inoue et al. 2003 Am J Respir Crit Care Med 167 50-6; Vargaftig and Singer 2003 Am J Physiol Lung Cell MoI Physiol 284 L260-9; Vargaftig and Singer 2003 Am J Respir Cell MoI Biol 28 410-9).

These effects of IL-13 are reproduced in transgenic mouse systems with either constitutive or inducible expression of IL-13 (Zhu, Homer et al. 1999 J Clin Invest 103 779-88; Zhu, Lee et al. 2001 Am J Respir Crit Care Med 164 S67-70; Lanone, Zheng et al. 2002 J Clin Invest 110463-74). Chronic transgenic over-expression of IL-13 also induces subepithelial fibrosis and emphysema. Mice deficient in the IL-13 (and IL-4) signaling molecule STAT6 fail to develop allergen-induced AHR and mucus overproduction (Kuperman, Huang et al. 2002 Nat Med 8 885-9). Studies using soluble IL-13 receptor fusion protein (sDL-13Ralpha2Fc) have demonstrated the pivotal role of this cytokine in experimental allergen ovalbumin (OVA)-induced airway disease (Grunig, Warnock et al. 1998 Science 282 2261-3; Wills-Karp, Luyimbazi et al. 1998 Science 282 2258-61; Taube, Duez et al. 2002 J Immunol 169 6482-9).

Efficacy of anti-IL-13 treatment was also demonstrated in a chronic model of murine asthma. In addition to exhibiting features of mucus hyper-secretion and AHR, this model of chronic asthma demonstrates several hallmarks of human disease that are lacking in the more acute models. These include eosinophilia of the lung tissue located in inter-epithelial spaces as well as smooth muscle fibrosis as measured by increases in collagen deposition. The chronic asthma model is induced with repeated aerosol challenges with OVA in OVA-sensitized mice 1x/week for a total of 4 weeks. Anti-IL-13 antibody administered for the final 2 weeks of OVA challenges (from day 36 with efficacy read-outs assessed on day 53 of study) significantly inhibited AHR, pulmonary inflammation, goblet cell hyperplasia, mucus hypersecretion, and airway fibrosis (Yang, Li et al. 2005 J Pharmacol Exp Ther).

The therapeutic effect of IL-13 antagonist was also demonstrated to inhibit AHR in a primate model of asthma, (American Thoracic Society, San Diego 2005).

IL-13 is implicated in the pathogenesis of human asthma as elevated levels of IL-13 mRNA and protein have been detected in lungs of asthmatic patients, which correlate with severity of the disease (Huang, Xiao et al. 1995 J Immunol 155 2688-94). In addition, human IL-13 genetic polymorphisms, which lead to elevated IL-13 levels, have been identified and are associated with asthma and atopy (Heinzmann, Mao et al. 2000 Hum Mol Genet 9 549-59; Hoerauf, Kruse et al. 2002 Microbes Infect 4 37-42; Vercelli 2002 Curr Opin Allergy Clin Immunol 2 389-93; Heinzmann, Jerkic et al. 2003 J Allergy Clin Immunol 112 735-9; Chen, Ericksen et al. 2004 J Allergy Clin Immunol 114 553-60; Vladich, Brazille et al. 2005 J Clin Invest), and elevated IL-13 levels have been detected in the lung of asthma patients (Huang, Xiao et al. 1995 J Immunol 155 2688-94; Arima, Umeshita-Suyama et al. 2002 J Allergy Clin Immunol 109 980-7; Berry, Parker et al. 2004 J Allergy Clin Immunol 114 1106-9). A genetic linkage between IL-13 and asthma has also been demonstrated as individuals with a polymorphism in the IL-13 gene which causes higher plasma IL-13 levels have an increased risk for atropy and asthma (Wills-Karp 2000 Respir Res 1 19-23).

Due to the role of human IL-13 in a variety of human disorders, therapeutic strategies have been designed to inhibit or counteract IL-13 activity. In particular, antibodies that bind to, and neutralize, IL-13 have been sought as a means to inhibit IL-13 activity. However, there exists a need in the art for suitable and/or improved antibodies capable of binding IL-13, especially human IL-13. In particular the antibodies are capable of neutralizing human IL-13. The present invention provides a novel family of binding proteins, CDR grafted antibodies, humanized antibodies, and fragments thereof, capable of binding human IL-13, binding with high affinity, and binding and neutralizing human IL-13.

SUMMARY OF THE INVENTION

This invention pertains to a novel IL-13 specific antibody and fragments, for example IL-13 binding fragments thereof, in particular neutralizing antibodies and fragments.

BRIEF DESCRIPTION OF THE DRAWINGS

FIG. 1 shows: the amino acid sequence for each of CDR 1, 2, 3 from the heavy chain (CDR H) and CDR 1, 2, 3 from the light chain (CDR L)
  the amino acid sequence for the rat antibody light chain variable region
  the DNA sequence for the rat antibody light chain variable region, and
  the amino acid sequence for the rat antibody light chain variable region with signal sequence FIG. 2 shows the DNA sequence for the rat antibody light chain variable region with signal sequence,
  the amino acid sequence for the rat antibody light chain variable and constant region
  the DNA sequence for the rat antibody light chain variable and constant region
  the amino acid sequence for the rat antibody light chain with signal sequence FIG. 3 shows the DNA sequence for the rat antibody light chain with signal sequence
  the amino acid sequence for the rat antibody heavy chain variable region
  the DNA sequence for the rat antibody heavy chain variable region
  the amino acid sequence for the rat antibody heavy chain variable region with signal sequence FIG. 4 shows the DNA sequence for the rat antibody heavy chain variable region with signal sequence
  the amino acid sequence for the rat antibody heavy chain variable and constant region FIG. 5 shows the DNA sequence for the rat antibody heavy chain variable and constant region
  the amino acid sequence for the rat antibody heavy chain variable and constant region with signal sequence FIG. 6 shows the DNA sequence for the rat antibody heavy chain variable and constant region with signal sequence FIG. 7 shows the amino acid sequence for the humanised antibody light chain variable region
  the DNA sequence for the humanised antibody light chain variable region
  the amino acid sequence for the humanised antibody light chain variable region with signal sequence
  the DNA sequence for the humanised antibody light chain variable region with signal sequence
  the amino acid sequence for the humanised antibody light chain variable and constant region FIG. 8 shows the DNA sequence for the humanised antibody light chain variable and constant region
  the amino acid sequence for the humanised antibody light chain variable and constant region with signal sequence
  the DNA sequence for the humanised antibody light chain variable and constant region with signal sequence FIG. 9 shows the amino acid sequence for the humanised antibody heavy chain variable region
  the DNA sequence for the humanised antibody heavy chain variable region
  the amino acid sequence for the humanised antibody heavy chain variable region with signal sequence
  the DNA sequence for the humanised antibody heavy chain variable region with signal sequence
  the amino acid sequence for the humanised antibody heavy chain variable and constant region FIG. 10 shows the DNA sequence for the humanised antibody heavy chain variable and constant region
  the amino acid sequence for the humanised antibody heavy chain variable and constant region with signal sequence
  the DNA sequence for the humanised antibody heavy chain variable and constant FIG. 11 shows amino acid and DNA sequences for human VK 1 2-1-(1)02 JK4 acceptor framework and VH2 3-1 2-26 JH4 acceptor framework FIG. 12 shows an alignment of the light chains for the rat, acceptor framework and the humanized light chains (SEQ ID NOs: 7, 29 and 23, respectively) and also heavy chains (SEQ ID NOs: 15, 41 and 31, respectively). CDRs are in bold and underlined. Donor residues G49 and R71 are in bold, italics and highlighted.

Figure 13:
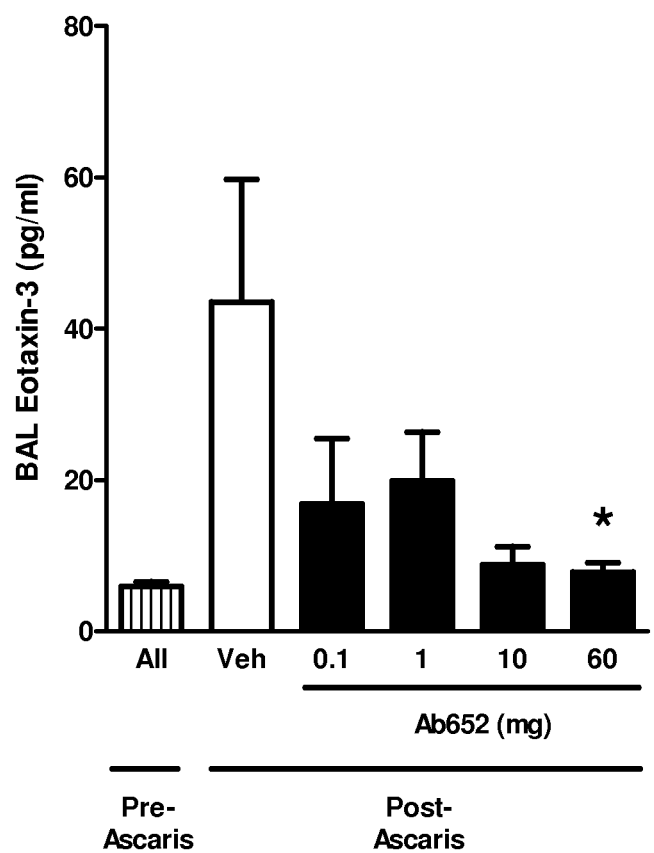
FIG. 13 Effect of Ab652 on BAL eotaxin-3 measured 24 h after allergen challenge. Data are expressed as mean±SEM, n=4-8 per group.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus 'CDR-H1', as used herein, comprises residues 26 to 35, as described by a combination of the Kabat numbering system and Chothia's topological loop definition.

The CDRs of the light chain variable domain are located at residues 24 to 34 CDR-L1), residues 50 to 56 (CDR-L2) and residues 89 to 97 (CDR-L3) according to the Kabat numbering system.

In one embodiment the antibody is an antagonistic antibody.

As used herein, the term 'antagonistic antibody' describes an antibody that is capable of inhibiting and/or neutralizing the biological signalling activity of IL-13, for example by blocking binding or substantially reducing binding of IL-13 to IL-13 receptor and thus inhibiting the activation of the receptor.

Antibodies for use in the present invention may be obtained using any suitable method known in the art. The IL-13 polypeptide, including a fusion polypeptide containing IL-13, or cells (recombinantly) expressing the polypeptide can be used to produce antibodies which specifically recognise IL-13. The IL-13 polypeptide may be the 'mature' polypeptide or a biologically active fragment or derivative thereof. IL-13 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The IL-13 polypeptide may in some instances be part of a larger protein such as a fusion protein for example fused to an affinity tag.

Antibodies generated against the IL-13 polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Antibodies for use in the present invention include whole antibodies and functionally active fragments or derivatives thereof and may be, but are not limited to, monoclonal, humanised, fully human or chimeric antibodies.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by for example the methods described by Babcook, J. et al., 1996, Proc. Natl. Acad. Sci. USA 93(15): 7843-78481; WO92/02551; WO2004/051268 and International Patent Application number WO2004/106377.

Screening for antibodies can be performed using assays to measure binding to IL-13 and/or assays to measure the ability to block the binding of IL-13 to one or more of it's receptors. An example of a binding assay is an ELISA, for example, using a fusion protein of IL-13, which is immobilized on plates, and employing a conjungated secondary antibody to detect anti-IL-13 antibody bound to the IL-13. An example of a blocking assay is a flow cytometry based assay measuring the blocking of IL-13 ligand protein binding to an IL-13R. A fluorescently labelled secondary antibody is used to detect the amount of IL-13 ligand protein binding to the IL-13R.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are composed of elements derived from two different species such that the element retains the characteristics of the species from which it is derived. Generally a chimeric antibody will comprise a variable region from one species, for example a mouse, rat, rabbit or similar and constant region from another species such as a human.

The antibodies for use in the present invention can also be generated using various. phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, but not necessarily from the same antibody. Examples of fully human antibodies may include antibodies produced, for example by the phage display methods described above and antibodies produced by mice in which the murine immunoglobulin variable and optionally the constant region genes have been replaced by their human counterparts eg. as described in general terms in EP 0546073, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 and EP 0463151.

In one embodiment the present invention provides an antagonistic antibody having specificity for human IL-13, comprising a heavy chain, wherein the variable domain of the heavy chain comprises at least one CDR having the sequence given in FIG. 1, SEQ ID NO:1 for CDR-H1, a CDR having the sequence given in SEQ ID NO:2 for CDR-H2 and/or a CDR having the sequence given in SEQ ID NO:3 for CDR-H3.

In another embodiment the present invention provides an antagonistic antibody having specificity for human IL-13, comprising a heavy chain, wherein at least two of CDR-H1, CDR-H2 and CDR-H3 of the variable domain of the heavy chain are selected from the following: the sequence given in SEQ ID NO:1 for CDR-H1, the sequence given in SEQ ID NO:2 for CDR-H2 and the sequence given in SEQ ID NO:3 for CDR-H3. For example, the antibody may comprise a heavy chain wherein CDR-H1 has the sequence given in SEQ ID NO:1 and CDR-H2 has the sequence given in SEQ ID NO:2. Alternatively, the antibody may comprise a heavy chain wherein CDR-H1 has the sequence given in SEQ ID NO:1 and CDR-H3 has the sequence given in SEQ ID NO:3, or the antibody may comprise a heavy chain wherein CDR-H2 has the sequence given in SEQ ID NO:2 and CDR-H3 has the sequence given in SEQ ID NO:3. For the avoidance of doubt, it is understood that all permutations are included.

In another embodiment the present invention provides an antagonistic antibody having specificity for human IL-13, comprising a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3.

In one embodiment the present invention provides an antagonistic antibody having specificity for human IL-13, comprising a light chain, wherein the variable domain of the light chain comprises at least one CDR having the sequence given in FIG. 1, SEQ ID NO:4 for CDR-L1, a CDR having the sequence given in SEQ ID NO:5 for CDR-L2 and/or a CDR having the sequence given in SEQ ID NO:6 for CDR-L3.

In another embodiment the present invention provides an antagonistic antibody having specificity for human IL-13, comprising a light chain, wherein at least two of CDR-L1, CDR-L2 and CDR-L3 of the variable domain of the light chain are selected from the following: the sequence given in SEQ ID NO:4 for CDR-L1, the sequence given in SEQ ID NO:5 for CDR-L2 and the sequence given in SEQ ID NO:6 for CDR-L3. For example, the antibody may comprise a light chain wherein CDR-L1 has the sequence given in SEQ ID NO:4 and CDR-L2 has the sequence given in SEQ ID NO:5. Alternatively, the antibody may comprise a light chain wherein CDR-L1 has the sequence given in SEQ ID NO:4 and CDR-L3 has the sequence given in SEQ ID NO:6, or the antibody may comprise a light chain wherein CDR-L2 has the sequence given in SEQ ID NO:5 and CDR-L3 has the sequence given in SEQ ID NO:6. For the avoidance of doubt, it is understood that all permutations are included.

In another embodiment the present invention provides an antagonistic antibody having specificity for human IL-13, comprising a light chain, wherein the variable domain comprises the sequence given in SEQ ID NO:4 for CDR-L1, the sequence given in SEQ ID NO:5 for CDR-L2 and the sequence given in SEQ ID NO:6 for CDR-L3.

The antibody molecules of the present invention suitably comprise a complementary light chain or a complementary heavy chain, respectively.

Hence in one embodiment, an antibody according to the present invention comprises a heavy chain, wherein the variable domain of the heavy chain comprises the sequence given in SEQ ID NO:1 for CDR-H1, the sequence given in SEQ ID NO:2 for CDR-H2 and/or the sequence given in SEQ ID NO:3 for CDR-H3 and a light chain wherein the variable domain of the light chain comprises the sequence given in SEQ ID NO:4 for CDR-L1, the sequence given in SEQ ID NO:5 for CDR-L2 and/or the sequence given in SEQ ID NO:6 for CDR-L3.

It will be appreciated that one or more amino acid substitutions, additions and/or deletions may be made to the CDRs provided by the present invention without significantly altering the ability of the antibody to bind to IL-13 and to neutralise IL-13 activity. The effect of any amino acid substitutions, additions and/or deletions can be readily tested by one skilled in the art, for example by using the methods described herein, particularly those illustrated in the Examples, to determine IL-13 binding and inhibition of the IL-13/IL-13 receptor interaction.

Accordingly, the present invention provides an antibody having specificity for human IL-13 comprising one or more CDRs selected from CDRH-1 (SEQ ID NO:1), CDRH-2 (SEQ ID NO:2), CDRH-3 (SEQ ID NO:3), CDRL-1 (SEQ ID NO:4), CDRL-2 (SEQ ID NO:5) and CDRL-3 (SEQ ID NO:6) in which one or more amino acids in one or more of the CDRs has been substituted with another amino acid, for example a similar amino acid as defined herein below.

In one embodiment, the present invention provides an antibody having specificity for human IL-13 comprising CDRH-1 (SEQ ID NO:1), CDRH-2 (SEQ ID NO:2 or SEQ ID NO:20), CDRH-3 (SEQ ID NO:3), CDRL-1 (SEQ ID NO:4), CDRL-2 (SEQ ID NO:5) and CDRL-3 (SEQ ID NO:6), for example in which one or more amino acids in one or more of the CDRs has been substituted with another amino acid, such as a similar amino acid as defined herein below.

In one embodiment, an antibody of the present invention comprises a heavy chain, wherein the variable domain of the heavy chain comprises three CDRs wherein the sequence of CDRH-1 has at least 60% identity or similarity to the sequence given in SEQ ID NO:1, CDRH-2 has at least 60% identity or similarity to the sequence given in SEQ ID NO:2 and/or CDRH-3 has at least 60% identity or similarity to the sequence given in SEQ ID NO:3. In another embodiment, an antibody of the present invention comprises a heavy chain, wherein the variable domain of the heavy chain comprises three CDRs wherein the sequence of CDRH-1 has at least 70%, 80%, 90%, 95% or 98% identity or similarity to the sequence given in SEQ ID NO:1, CDRH-2 has at least 70%, 80%, 90%, 95% or 98% identity or similarity to the sequence given in SEQ ID NO:2 and/or CDRH-3 has at least 70%, 80%, 90%, 95% or 98% identity or similarity to the sequence given in SEQ ID NO:3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

In another embodiment, an antibody of the present invention comprises a light chain, wherein the variable domain of the light chain comprises three CDRs wherein the sequence of CDRL-1 has at least 60% identity or similarity to the sequence given in SEQ ID NO:4, CDRL-2 has at least 60% identity or similarity to the sequence given in SEQ ID NO:5 and/or CDRL-3 has at least 60% identity or similarity to the sequence given in SEQ ID NO:6. In another embodiment, an antibody of the present invention comprises a light chain, wherein the variable domain of the light chain comprises three CDRs wherein the sequence of CDRL-1 has at least 70%, 80%, 90%, 95% or 98% identity or similarity to the sequence given in SEQ ID NO:4, CDRL-2 has at least 70%, 80%, 90%, 95% or 98% identity or similarity to the sequence given in SEQ ID NO:5 and/or CDRL-3 has at least 70%, 80%, 90%, 95% or 98% identity or similarity to the sequence given in SEQ ID NO:6.

In one embodiment the antibody provided by the present invention is a monoclonal antibody.

In one embodiment the antibody provided by the present invention is a chimeric antibody.

In one embodiment the antibody provided by the present invention is a CDR-grafted antibody molecule comprising one or more of the CDRs provided in SEQ ID NOS:1, 2, 3, 4, 5, 6 or variants thereof. As used herein, the term 'CDR-grafted antibody molecule' refers to an antibody molecule wherein the heavy and/or light chain contains one or more CDRs (including, if desired, one or more modified CDRs) from a donor antibody (e.g. a murine or rat monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human framework which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and light chain. Alternatively, human germline sequences may be used; these are available at: vbase.mrc-cpe.cam.ac.uk/.

In a CDR-grafted antibody of the present invention, the acceptor heavy and light chains do not necessarily need to be derived from the same antibody and may, if desired, comprise composite chains having framework regions derived from different chains.

The suitable framework region for the heavy chain of the CDR-grafted antibody of the present invention is derived from the human sub-group VH2 sequence 3-1 2-26 together with JH4 (SEQ ID NO:41). Accordingly, provided is a neutralising CDR-grafted antibody comprising at least one non-human donor CDR wherein the heavy chain framework region is derived from the human subgroup VH2 sequence 3-1 2-26 together with JH4. The sequence of human JH4 is as follows: (YFDY)WGQGTLVTVS (Seq ID No: 43). The YFDY motif is part of CDR-H3 and is not part of framework 4 (Ravetch, J V. et al., 1981, Cell, 27, 583-591).

The suitable framework region for the light chain of the CDR-grafted antibody of the present invention is derived from the human germline sub-group VK1 sequence 2-1 1-02 together with JK4 (SEQ ID NO:39). Accordingly, provided is a neutralizing CDR-grafted antibody comprising at least one non-human donor CDR wherein the light chain framework region is derived from the human subgroup sequence 2-1 1-02 together with JK4. The JK4 sequence is as follows: (LT)FGGGTKVEIK (Seq ID No: 44). The LT motif is part of CDR-L3 and is not part of framework 4 (Hieter, P A., et al., 1982, J. Biol. Chem., 257, 1516-1522).

In one embodiment a light and/or heavy framework is selected from a sequence as shown in SEQ ID No: 39 to 42.

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Suitably, in a CDR-grafted antibody molecule of the present invention, if the acceptor heavy chain has the human VH2 sequence 3-12-26 together with JH4, then the acceptor framework regions of the heavy chain comprise, in addition to one or more donor CDRs, a donor residue at at least one of positions 49 and 71 (according to Kabat et al., (supra)) (See FIG. 12).

Accordingly, provided is a CDR-grafted antibody, wherein at least the residues at positions 49 and 71 of the variable domain of the heavy chain are donor residues.

Donor residues are residues from the donor antibody, i.e. the antibody from which the CDRs were originally derived. Preferably the residues are Glycine and Arginine at positions 49 and 71 respectively.

In one embodiment, an antibody of the present invention comprises a heavy chain, wherein the variable domain of the heavy chain comprises the sequence given in SEQ ID NO: 31

It will be appreciated that one or more amino acid substitutions, additions and/or deletions may be made to the antibody variable domains, provided by the present invention, without significantly altering the ability of the antibody to bind to IL-13 and to neutralize IL-13 activity. The effect of any amino acid substitutions, additions and/or deletions can be readily tested by one skilled in the art, for example by using the methods described in the Examples to determine IL-13 binding and/or ligand/receptor blocking.

In another embodiment, an antibody of the present invention comprises a heavy chain, wherein the variable domain of the heavy chain comprises a sequence having at least 60% identity or similarity to the sequence given in SEQ ID NO:31. In one embodiment, an antibody of the present invention comprises a heavy chain, wherein the variable domain of the heavy chain comprises a sequence having at least 70%, 80%, 90%, 95% or 98% identity or similarity to the sequence given in SEQ ID NO: 31.

In one embodiment, an antibody of the present invention comprises a light chain, wherein the variable domain of the light chain comprises the sequence given in SEQ ID NO: 23.

In another embodiment, an antibody of the present invention comprises a light chain, wherein the variable domain of the light chain comprises a sequence having at least 60% identity or similarity to the sequence given in SEQ ID NO:23. In one embodiment the antibody of the present invention comprises a light chain, wherein the variable domain of the light chain comprises a sequence having at least 70%, 80%, 90%, 95% or 98% identity or similarity to the sequence given in SEQ ID NO: 23.

In one embodiment an antibody of the present invention comprises a heavy chain, wherein the variable domain of the heavy chain comprises the sequence given in SEQ ID NO:31 and a light chain, wherein the variable domain of the light chain comprises the sequence given in SEQ ID NO:23.

In another embodiment of the invention, the antibody comprises a heavy chain and a light chain, wherein the variable domain of the heavy chain comprises a sequence having at least 60% identity or similarity to the sequence given in SEQ ID NO:31 and the variable domain of the light chain comprises a sequence having at least 60% identity or similarity to the sequence given in SEQ ID NO:23. Suitably, the antibody comprises a heavy chain, wherein the variable domain of the heavy chain comprises a sequence having at least 70%, 80%, 90%, 95% or 98% identity or similarity to the sequence given in SEQ ID NO:31 and a light chain, wherein the variable domain of the light chain comprises a sequence having at least 70%, 80%, 90%, 95% or 98% identity or similarity to the sequence given in SEQ ID NO:23.

The antibody molecules of the present invention may comprise a complete antibody molecule having full length heavy and light chains or a fragment thereof and may be, but are not limited to Fab, modified Fab, Fab', modified Fab', F(ab')$_2$, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO 2005/003169, WO 2005/003170 and WO 2005/003171 and Fab-dAb fragments described in International patent application WO2009/040562. Multi-valent antibodies may comprise multiple specificities or may be monospecific (see for example WO 92/22853 and WO 05/113605).

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking IL-13 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995). However, there is no C-terminal Lysine on either heavy or light chain of Ab652 embodiment of the invention.

In one embodiment the antibody heavy chain comprises a CH1 domain and the antibody light chain comprises a CL domain, either kappa or lambda.

In one embodiment the antibody provided by the present invention is an antagonistic antibody having specificity for human IL-13 in which the heavy chain constant region comprises a modified hinge region. Accordingly, the present invention provides an antibody in which the heavy chain comprises or consists of the sequence given in SEQ ID No: 35

It will be appreciated that one or more amino acid substitutions, additions and/or deletions may be made to the antibody variable and/or constant domains provided by the present invention without significantly altering the ability of the antibody to bind to IL-13 and to neutralize IL-13 activity. The effect of any amino acid substitutions, additions and/or deletions can be readily tested by one skilled in the art, for example by using the methods described herein, particularly those illustrated in the Examples, to determine IL-13 binding and blocking of the IL-13/IL-13 receptor interaction.

In one embodiment of the invention, the antibody comprises a heavy chain, wherein the heavy chain comprises a sequence having at least 60% identity or similarity to the sequence given in SEQ ID NO: 35. Suitably, the antibody comprises a heavy chain, wherein the heavy chain comprises a sequence having at least 70%, 80%, 90%, 95% or 98% identity or similarity to the sequence given in SEQ ID NO: 35.

In one embodiment an antibody molecule according to the present invention comprises a light chain comprising the sequence given in SEQ ID NO: 27.

In one embodiment of the invention, the antibody comprises a light chain, wherein the light chain comprises a sequence having at least 60% identity or similarity to the sequence given in SEQ ID NO: 27. For example, the antibody comprises a light chain, wherein the light chain comprises a sequence having at least 70%, 80%, 90%, 95% or 98% identity or similarity to the sequence given in SEQ ID NO: 27.

In one embodiment the present invention provides an antibody in which the heavy chain comprises or consists of the sequence given in SEQ ID NO:35 and the light chain comprises or consists of the sequence given in SEQ ID NO:27.

In one embodiment of the invention, the antibody comprises a heavy chain and a light chain, wherein the heavy chain comprises a sequence having at least 60% identity or similarity to the sequence given in SEQ ID NO:35 and the light chain comprises a sequence having at least 60% identity or similarity to the sequence given in SEQ ID NO:27. Generally, the antibody comprises a heavy chain, wherein the heavy chain comprises a sequence having at least 70%, 80%, 90%, 95% or 98% identity or similarity to the sequence given in SEQ ID NO:35 and a light chain, wherein the light chain comprises a sequence having at least 70%, 80%, 90%, 95% or 98% identity or similarity to the sequence given in SEQ ID NO:27.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or surface carries no net electrical charge. In one embodiment the antibody or fragment according to the present disclosure has an isoelectric point (pI) of at least 7. In one embodiment the antibody or fragment has an isoelectric point of at least 8, such as 8.5, 8.6, 8.7, 8.8 or 9. In one embodiment the pI of the antibody is 8.

The IL-13 antibody and fragments of the invention may be engineered to have an appropriate isoelectric point. This may lead to antibodies and/or fragments with more robust properties, in particular suitable solubility and/or stability profiles.

Thus in one aspect the invention provides a humanised IL-13 antibody engineered to have an isoelectric point different to that of the originally identified antibody. The antibody may, for example be engineered by replacing an amino acid residue such as replacing an acidic amino acid residue with one or more basic amino acid residues. Alternatively, basic amino acid residues may be added or acidic amino acid residues can be removed. Alternatively, if the molecule has an unacceptably high pI value acidic residues may be introduced to lower the pH, as required. The pI of the engineered antibody or fragment may, for example be 8 or above, such 8.5 or 9. It is important that when manipulating the pI, then care must be taken to retain the desirable activity of the antibody or fragment. Thus in one embodiment the engineered antibody or fragment has the same or substantially the same activity as the "unmodified" antibody or fragment.

Programs such as **ExPASY www.expasy.ch/tools/pi_tool.html, and http://www.iut-arles.up.univ-mrs.fr/w3bb/d_abim/compo-p.html, may be used to predict the isoelectric point of the antibody or fragment.

In one embodiment the antibodies of the present invention are suitable for inhaled delivery, for example, by nebulisation. In one example the physical properties of the antibodies of the present invention e.g. binding affinity and potency are not substantially altered by nebulisation. In one example the antibodies of the present invention are highly stable. One measure of antibody stability is melting temperature (Tm). Melting temperature may be determined by any suitable method known in the art, for example using Thermofluor (Ericsson et al, Analytical Biochemistry 357 (2006) 289-298) or DSC (differential scanning calorimetry). Preferably the antibodies provided by the present invention have a high melting temperature (Tm), typically of at least 75° C. In one example the antibody of the present invention has a Tm of at least 75° C. In one example the antibody of the present invention has a Tm of at least 80° C. In one example the antibody of the present invention has a Tm of at least 83° C.

Also provided by the present invention is a specific region or epitope of human IL-13 which is bound by an antibody provided by the present invention, in particular an antibody comprising the heavy chain sequence (SEQ ID NO:35) and/or the light chain sequence (SEQ ID NO:27).

This specific region or epitope of the human IL-13 polypeptide can be identified by any suitable epitope mapping method known in the art in combination with any one of the antibodies provided by the present invention. Examples of such methods include screening peptides of varying lengths derived from IL-13 for binding to the antibody of the present invention with the smallest fragment that can specifically bind to the antibody containing the sequence of the epitope recognised by the antibody. The IL-13 peptides may be produced synthetically or by proteolytic digestion of the IL-13 polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antagonistic antibodies which bind the same epitope.

Antibodies which cross-block the binding of an antibody according to the present invention in particular, an antibody comprising the heavy chain sequence (SEQ ID NO:31) and the light chain sequence (SEQ ID NO:27) may be similarly useful in antagonising IL-13 activity. Accordingly, the present invention also provides an antagonistic antibody having specificity for human IL-13, which cross-blocks the binding of any one of the antibodies described above to human IL-13 and/or is cross-blocked from binding IL-13 by any one of those antibodies. In one embodiment, such an antibody binds to the same epitope as an antibody described herein above. In another embodiment the cross-blocking neutralizing antibody binds to an epitope which borders and/or overlaps with the epitope bound by an antibody described herein above. In another embodiment the cross-blocking neutralizing antibody of this aspect of the invention does not bind to the same epitope as an antibody of the present invention or an epitope that borders and/or overlaps with said epitope.

Cross-blocking antibodies can be identified using any suitable method in the art, for example by using competition ELISA or BIAcore assays where binding of the cross blocking antibody to human IL-13 prevents the binding of an antibody of the present invention or vice versa.

In one embodiment there is provided an antagonistic antibody having specificity for human IL-13, which cross-blocks the binding of an antibody whose heavy chain comprises the sequence shown in SEQ ID NO: 35 and whose light chain comprises the sequence shown in SEQ ID NO: 27 to human IL-13. In one embodiment the cross-blocking antibodies provided by the present invention inhibit the binding of an antibody comprising the heavy chain sequence shown in SEQ ID NO:35 and the light chain sequence shown in SEQ ID NO:27 by greater than 80%, for example by greater than 85%, such as by greater than 90%, in particular by greater than 95%.

Alternatively or in addition, antagonistic antibodies according to this aspect of the invention may be cross-blocked from binding to human IL-13 by an antibody comprising the heavy chain sequence shown in SEQ ID NO:35 and the light chain sequence shown in SEQ ID NO: 27. Also provided therefore is an antagonistic antibody molecule having specificity for human IL-13 which is cross-blocked from binding human IL-13 by an antibody comprising the heavy chain sequence shown in SEQ ID NO: 35 and the light chain sequence shown in SEQ ID NO: 27. In one embodiment the antagonistic antibodies provided by this aspect of the invention are inhibited from binding human IL-13 by an antibody comprising the heavy chain sequence shown in SEQ ID NO: 35 and the light chain sequence shown in SEQ ID No: 27 by greater than 80%, for example by greater than 85%, such as by greater than 90%, in particular by greater than 95%.

In one embodiment the cross-blocking antibodies provided by the present invention are fully human. In one embodiment the cross-blocking antibodies provided by the present invention are humanised. In one embodiment the cross-blocking antibodies provided by the present invention have an affinity for human IL-13 of 100 pM or better. In one embodiment the cross-blocking antibodies provided by the present invention have an affinity for human IL-13 of 50 pM or better.

In one embodiment the cross-blocking antibody has an isoelectric point of at least 7, for example at least 8, such as 8.5, 8.6, 8.7, 8.8, 8.9 or 9.0.

The antibody molecules of the present invention suitably have a high binding affinity, in particular picomolar affinity. Affinity may be measured using any suitable method known in the art, including by surface Plasmon resonance, including BIAcore as described in the Examples herein using isolated natural or recombinant IL-13. In one example affinity is measured using recombinant human IL-13 as described in the Examples herein. In one embodiment the antibody molecule of the present invention has a binding affinity of about 100 pM or better. In one embodiment the antibody molecule of the present invention has a binding affinity of about 50 pM or better. In one embodiment the antibody molecule of the present invention has a binding affinity of about 40 pM or better. In one embodiment the antibody molecule of the present invention has a binding affinity of about 30 pM or better. In one embodiment the antibody molecule of the present invention has a binding affinity of about 20 pM or better. In one embodiment the antibody molecule of the present invention is fully human or humanised and has a binding affinity of about 100 pM or better. In one embodiment the antibody molecule of the present invention is fully human or humanised and has a binding affinity of 30 pM or better.

It will be appreciated that the affinity of antibodies provided by the present invention may be altered using any suitable method known in the art. The present invention therefore also relates to variants of the antibody molecules of the present invention, which have an improved affinity for IL-13. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of *E. coli* (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention block the interaction between IL-13 and an IL-13 receptor, in particular the antibody molecules of the present invention block the interaction between IL-13 and IL-13Rα1 and the interaction between IL-13 and IL-13 Rα2. Numerous assays suitable for determining the ability of an antibody to block this interaction are described in the examples herein. In one embodiment the present invention provides a neutralising antibody having specificity for human IL-13. In one embodiment the human IL-13 receptor used in the assay is natural human IL-13 Rα1 or natural human IL-13Rα2. In one embodiment the human IL-13 receptor used in the assay is recombinant human IL-13 Rα1 or recombinant human IL-13Rα2. In one embodiment the human IL-13 used in the assay is recombinant human IL-13. In one embodiment the neutralising antibody is a humanised or fully human antibody or fragment thereof.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO 03031581. Alternatively, where the effector molecule is a protein or polypeptide the linkage may be achieved using recombinant DNA procedures, for example as described in WO 86/01533 and EP 0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO 05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,667,425; WO 98/25971). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules may be covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, the antibody is a modified Fab fragment or diFab which is PEGylated, i.e. has PEG (poly (ethyleneglycol)) covalently attached thereto, e.g. according to the method disclosed in EP 0948544 or EP 1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides an antagonistic antibody molecule having specificity for human IL-13, which is a modified Fab' fragment having a heavy chain comprising the sequence given in SEQ ID NO:35 and a light chain comprising the sequence given in SEQ ID NO:27 and having at the C-terminal end of its heavy chain a modified hinge region containing at least one cysteine residue to which an effector molecule is attached. Suitably the effector molecule is PEG and is attached using the methods described in (WO 98/25971 and WO 2004072116 or in WO 2007/003898. Effector molecules may be attached to antibody fragments using the methods described in International patent applications WO 2005/003169, WO 2005/003170 and WO 2005/003171.

In one embodiment the antibody or fragment is not attached an effector molecule.

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof.

DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided herein. A suitable signal peptide for the heavy chain may be encoded therein such as the murine signal peptide MEWSWVFLFF LSVTTGVHS (SEQ ID NO: 45). A suitable signal peptide for the light chain may be encoded therein such as the murine signal peptide MSVPTQVLGL LLLWLTDARC (SEQ ID NO: 46) which is cleaved to give an antagonistic antibody molecule of the present invention. The present invention also provides an isolated DNA sequence encoding the heavy chain of an antibody of the present invention which comprises SEQ ID NO: 32, 34 or 36 or 38. The present invention also provides an isolated DNA sequence encoding the light chain of an antibody of the present invention which comprises SEQ ID NO:24, 26, 28 or 30.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments appear to optimised and conducive to commercial processing.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody, fragment or composition according to the disclosure is employed in combination with a further pharmaceutically active agent, for example a corticosteroid (such as fluticasone propionate) and/or a beta-2-agonist (such as salbutamol, salmeterol or formoterol) or inhibitors of cell growth and proliferation (such as rapamycin, cyclophosphmide, methotrexate) or alternatively a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

In one embodiment, in formulations according to the present disclosure, the pH of the final formulation is not similar to the value of the isoelectric point of the antibody or fragment, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared. Preferably the antibody molecules of the present invention are administered subcutaneously, by inhalation or topically.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases (such as nebulisable solutions or suspensions). Inhalable powders according to the disclosure containing the active substance may consist solely of the abovementioned active substances or of a mixture of the above mentioned active substances with physiologically acceptable excipient.

These inhalable powders may include monosaccharides (e.g. glucose or arabinose), disaccharides (e.g. lactose, saccharose, maltose), oligo- and polysaccharides (e.g. dextrans), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active (such as the antibody or fragment is of primary importance).

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

In one embodiment the formulation is provided as discrete ampoules containing a unit dose for delivery by nebulisation.

In one embodiment the antibody is supplied in lyophilised form, for reconstitutions or alternatively as a suspension formulation.

The antibody of the invention can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The antibodies of the present disclosure are thought to be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule (or compositions comprising same) for use in the control of inflammatory diseases, for example acute or chronic inflammatory disease. Suitably, the antibody molecule (or compositions comprising same) can be used to reduce the inflammatory process or to prevent the inflammatory process. In one embodiment there is provided an in vivo reduction of activated T cells, in particular those involved in inappropriate inflammatory immune responses, for example recruited to the vicinity/location of such a response.

Reduction of activated T cells, as employed herein, may be a reduction, 10, 20, 30, 40, 50, 60, 70, 80, 90 or more percent in comparison before treatment or without treatment.

Advantageously, treatment with an antibody, fragment or composition according to the present invention, may allow the reduction in the level of activated T cells, without reducing the patients general level of T cells (unactivated T cells). This may result in fewer side effects, and possibly prevent T cell depletion in the patient.

The present invention also provides the antibody molecule of the present invention for use in the treatment or prophylaxis of a pathological disorder that is mediated by IL-13 or associated with an increased level of IL-13.

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia.

The present invention also provides an antibody molecule according to the present invention for use in the treatment or prophylaxis of pain, particularly pain associated with inflammation.

In one embodiment the antibody according to the invention reduces resistance to treatment of inflammation, particularly lung resistance to treatment of inflammation.

In one embodiment the antibody according to the invention reduces IL-13 protein levels in bronchial tissue, for example in comparison to the levels before treatment. The reduction may be 5, 10, 20, 30, 40% or more.

In one embodiment the antibody according to the invention reduces IL-13 protein levels in nasal lavage fluid and/or bronchoalveolar fluid, for example in comparison to the levels before treatment. The reduction may be 5, 10, 20, 30, 40% or more.

In one embodiment the antibody according to the invention reduces eosinophil influx, for example in comparison to the levels before treatment. The reduction may be 5, 10, 20, 30, 40% or more, for example when treated for 1, 2, 3, 4, 5, 6 or more weeks.

In one embodiment the antibody according to the invention is suitable for reducing inappropriate levels of goblet cells, for example in the treatment of goblet cell hyperplasia, such as chronic goblet cell hyperplasia. The reduction may be observed after treatment for 1, 2, 3, 4, 5, 6 or more weeks.

In one embodiment the antibody according to the invention is suitable for reducing the levels of exhaled nitric oxide (FeNO), in comparison to levels before treatment. Exhaled nitric oxide is thought to be a risk factor or marker for lung inflammation.

In one embodiment the antibody according to the invention is suitable for prevention of inappropriate collagen deposition associated with inflammatory responses, in particular peribronchial collagen deposition.

In one embodiment the antibody according to the invention is suitable for preventing inappropriate angiogenesis associated with inflammatory responses.

Thus there is provided an antibody according to the invention for use in treatment and methods of treatment employing same.

Antibody according to the invention as employed herein also refers to fragments and derivatives disclosed in the specification.

The present invention further provides the use of an antibody molecule, fragment or composition according to the present invention in the manufacture of a medicament for the treatment or prophylaxis of a pathological disorder that is mediated by IL-13 or associated with an increased level of IL-13, for example as described herein, in particular the pathological disorder is rheumatoid arthritis, asthma or COPD.

The present invention further provides the use of an antibody molecule, fragment or composition according to the present invention in the manufacture of a medicament for the treatment or prophylaxis of one or more medical indications described herein.

An antibody molecule, fragment or composition of the present invention may be utilised in any therapy where it is desired to reduce the effects of IL-13 in the human or animal body. IL-13 may be circulating in the body or may be present in an undesirably high level localised at a particular site in the body, for example a site of inflammation.

In one embodiment the antibody molecule of the present invention or a composition comprising the same is used for the control of inflammatory disease, for example as described herein.

The present invention also provides a method of treating human or animal subjects suffering from or at risk of a disorder mediated by IL-13, the method comprising administering to the subject an effective amount of the antibody molecule of the present invention, or a composition comprising the same. In one example the antibody molecule is administered by inhalation.

In one example the disorder is selected from any of the medical indications provided above. In one example the disorder is selected from the group consisting of: asthmatic disorders, atopic disorders, chronic obstructive pulmonary disease (COPD), conditions involving airway inflammation, eosinophilia, fibrosis and excess mucus production, inflammatory conditions, autoimmune conditions, tumors or cancers, viral infection and suppression of expression of protective type 1 immune responses.

In one embodiment there is provided a process for purifying an antibody (in particular an antibody or fragment according to the invention).

In one embodiment there is provided a process for purifying an antibody (in particular an antibody or fragment according to the invention) comprising the steps:
performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

Thus in one embodiment there is provided a purified IL-13 antibody or fragment, for example a humanised antibody or fragment, in particular an antibody or fragment according to the invention, in substantially purified from, in particular free or substantially free of endotoxin and/or host cell protein or DNA. Having said this, the antibodies according to the present invention will generally be prepared in mammalian cells and thus endotoxin content is not generally an issue. In fact endotoxin content is more a consideration when the antibodies are prepared in bacterial cells.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

The antibody molecule of the present invention may also be used in diagnosis, for example in the in vivo diagnosis and imaging of disease states involving IL-13.

Suitable in vivo assays for testing the properties of the antibodies according to the invention include: the chronic house mite model, hyperresponsiveness to methacholine and/or the ovalbumin model of allergic lung inflammation.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures, in which:

FIG. 1 shows: the amino acid sequence for each of CDR 1, 2, 3 from the heavy chain (CDR H) and CDR 1, 2, 3 from the light chain (CDR L) (SEQ ID NOs 1-6)
    the amino acid sequence for the rat antibody light chain variable region (SEQ ID NO:7)
    the DNA sequence for the rat antibody light chain variable region (SEQ ID NO:8), and
    the amino acid sequence for the rat antibody light chain variable region with signal sequence (SEQ ID NO:9)

FIG. 2 shows the DNA sequence for the rat antibody light chain variable region with signal sequence (SEQ ID NO:10)
    the amino acid sequence for the rat antibody light chain variable and constant region (SEQ ID NO:11)
    the DNA sequence for the rat antibody light chain variable and constant region (SEQ ID NO:12)
    the amino acid sequence for the rat antibody light chain with signal sequence (SEQ ID NO:13)

FIG. 3 shows the DNA sequence for the rat antibody light chain with signal sequence (SEQ ID NO:14)
    the amino acid sequence for the rat antibody heavy chain variable region (SEQ ID NO:15)
    the DNA sequence for the rat antibody heavy chain variable region (SEQ ID NO:16)
    the amino acid sequence for the rat antibody heavy chain variable region with signal sequence (SEQ ID NO:17)

FIG. 4 shows the DNA sequence for the rat antibody heavy chain variable region with signal sequence (SEQ ID NO:18)
    the amino acid sequence for the rat antibody heavy chain variable and constant region (SEQ ID NO:19)

FIG. 5 shows the DNA sequence for the rat antibody heavy chain variable and constant region (SEQ ID NO:20)
    the amino acid sequence for the rat antibody heavy chain variable and constant region with signal sequence (SEQ ID NO:21)

FIG. 6 shows the DNA sequence for the rat antibody heavy chain variable and constant region with signal sequence (SEQ ID NO:22)

FIG. 7 shows the amino acid sequence for the humanised antibody light chain variable region (SEQ ID NO:23)
    the DNA sequence for the humanised antibody light chain variable region (SEQ ID NO:24)
    the amino acid sequence for the humanised antibody light chain variable region with signal sequence (SEQ ID NO:25)
    the DNA sequence for the humanised antibody light chain variable region with signal sequence (SEQ ID NO:26)
    the amino acid sequence for the humanised antibody light chain variable and constant region (SEQ ID NO:27)

FIG. 8 shows the DNA sequence for the humanised antibody light chain variable and constant region (SEQ ID NO:28)
    the amino acid sequence for the humanised antibody light chain variable and constant region with signal sequence (SEQ ID NO:29)
    the DNA sequence for the humanised antibody light chain variable and constant region with signal sequence (SEQ ID NO:30)

FIG. 9 shows the amino acid sequence for the humanised antibody heavy chain variable region (SEQ ID NO:31)

the DNA sequence for the humanised antibody heavy chain variable region (SEQ ID NO:32)

the amino acid sequence for the humanised antibody heavy chain variable region with signal sequence (SEQ ID NO:33)

the DNA sequence for the humanised antibody heavy chain variable region with signal sequence (SEQ ID NO:34)

the amino acid sequence for the humanised antibody heavy chain variable and constant region (SEQ ID NO:35)

FIG. 10 shows the DNA sequence for the humanised antibody heavy chain variable and constant region (SEQ ID NO:36)

the amino acid sequence for the humanised antibody heavy chain variable and constant region with signal sequence (SEQ ID NO:37)

the DNA sequence for the humanised antibody heavy chain variable and constant region (SEQ ID NO:38)

FIG. 11 shows amino acid and DNA sequences for human VK 1 2-1-(1)02 JK4 acceptor framework (SEQ ID NO:39 and SEQ ID NO:40) and VH2 3-1 2-26 JH4 acceptor framework (SEQ ID NO:41 and SEQ ID NO:42)

FIG. 12 shows an alignment of the light chains for the rat, acceptor framework and the humanised light chains and also heavy chains. CDRs are in bold and underlined.

Donor residues G49 and R71 are in bold, italic and highlighted.

FIG. 13 Effect of Ab652 on BAL eotaxin-3 measured 24 h after allergen challenge in a non-human primate model of asthma. Data are expressed as mean±SEM, n=4-8 per group.

Figure 14:
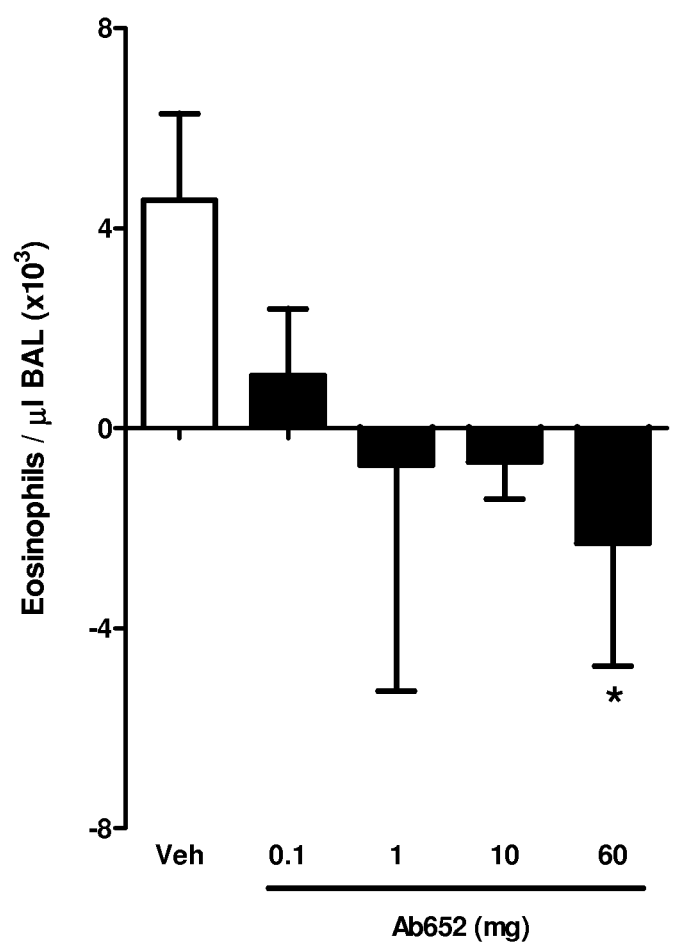
FIG. 14. Effect of Ab652 on the BAL eosinophil count measured 24 h after allergen challenge. Data are normalized to the BAL eosinophil count measured in the screening phase of the study. Mean±SEM, n=4-8 per group.

FIG. 14. Effect of Ab652 on the BAL eosinophil count measured 24 h after allergen challenge in a non-human primate model of asthma. Data are normalized to the BAL eosinophil count measured in the screening phase of the study. Mean±SEM, n=4-8 per group.

Figure 15:
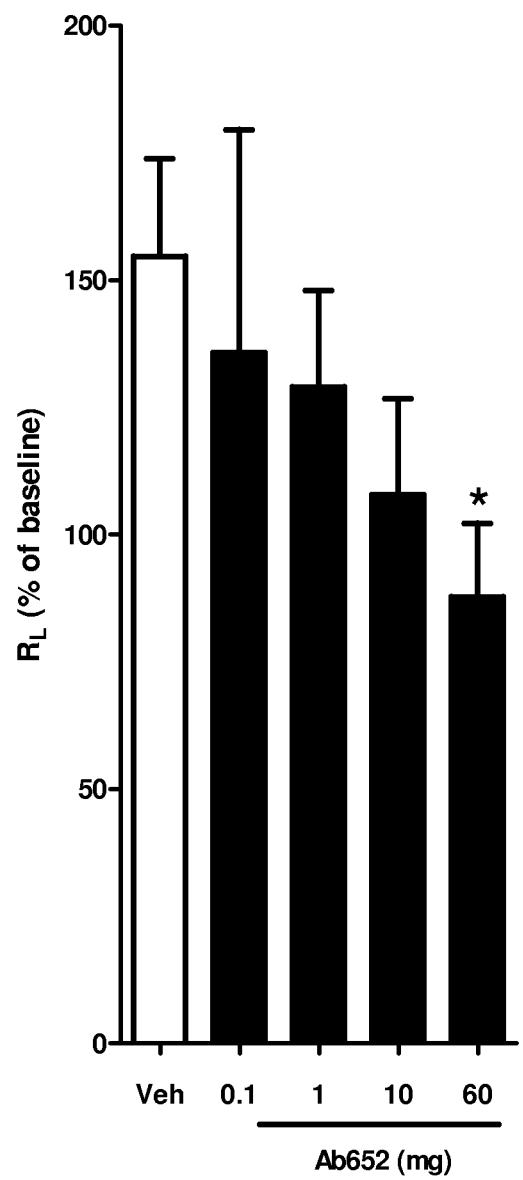
FIG. 15. Effect of Ab652 on peak airway resistance measured up to 15 minutes after allergen challenge. Data are expressed as mean±SEM, n=4-8 per group.

FIG. 15. Effect of Ab652 on peak airway resistance measured up to 15 minutes after allergen challenge in a non-human primate model of asthma. Data are expressed as mean±SEM, n=4-8 per group.

Figure 16:
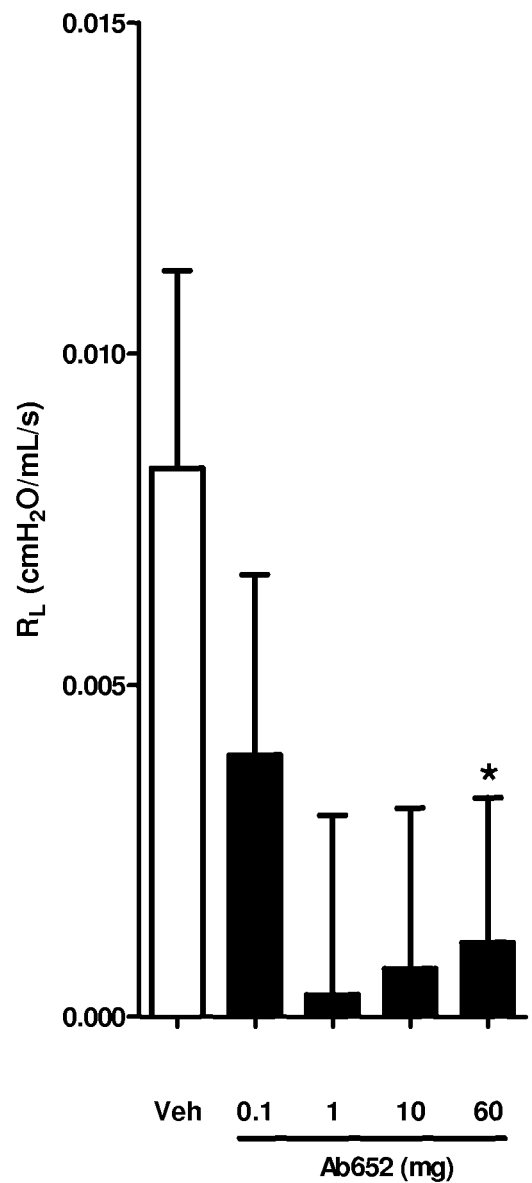
FIG. 16. Effect of Ab652 on airway resistance measured 24 h after allergen challenge. Data are normalized to airway resistance measured before exposure to allergen. Mean±SEM, n=4-8 per group.

FIG. 16. Effect of Ab652 on airway resistance measured 24 h after allergen challenge in a non-human primate model of asthma. Data are normalized to airway resistance measured before exposure to allergen. Mean±SEM, n=4-8 per group.

EXAMPLES

1. Therapeutic Antibody Generation/Selection

Rats were immunised with either purified human IL-13 (Peprotech) or rat fibroblasts expressing human IL-13 (expressing approx 1 ug/ml in culture supernatant), or in some cases, a combination of the two. Following 3 to 6 shots, animals were sacrificed and PBMC, spleen, bone marrow and lymph nodes harvested. Sera was monitored for binding to human IL-13 in ELISA and also for the ability to neutralize hIL-13 in the HEK-293 STAT-6 reporter cell assay (HEK-Blue assay, Invivogen).

SLAM cultures (B cell cultures) were prepared by a method similar to that described by Zubler et al. (J. Immunol. 1985). Briefly, 500-5000 splenocytes or PBMC from an immunised animal were cultured in batches of hundred 96-well plates with 200 μl/well RPMI 1640 medium (Gibco BRL) supplemented with 10% FCS (PAA laboratories ltd), 2% HEPES (Sigma Aldrich), 1% L-glutamine (Gibco BRL), 1% penicillin/streptomycin solution (Gibco BRL), 0.1% β-mercaptoethanol (Gibco BRL), 3% activated rabbit splenocyte culture supernatant and gamma-irradiated EL-4-B5 murine thymoma cells (5×10^4/well) for 7 days at 37° C. in an atmosphere of 5% CO2. B cell culture supernatants were tested in screening assays and positive supernatants consolidated into masterplates. Cultured B cells were frozen at −80° C. in 100 μl 10% DMSO in FCS.

SLAM culture supernatants were first screened for their ability to bind hIL-13 in a bead-based assay in the FMAT. This was a homogeneous assay using biotinylated human IL-13 coated onto streptavidin beads and a goat anti-rat Fc-Cy5 conjugate. Positives from this assay were then fed into the HEK-293 IL-13R-STAT-6 reporter cell assay (HEK-Blue assay, Invivogen) to identify neutralizers. Neutralizing supernatants were then profiled in the Biacore to estimate off-rate and also to characterise the mode of action of neutralisation. Neutralisation was categorised as either bin 1 or bin 2. Bin 1 represented an antibody that binds to human IL-13 and prevents binding of IL-13Rα1 and as a result also blocks IL-4R from binding. Bin 2 represented an antibody that binds hIL-13 in such a way that allows binding to IL-13Rα1 but prevents recruitment of IL-4R into the complex. We were selecting antibodies that operated via bin 1.

Approx. 7500 IL-13-specific positives were identified in the primary FMAT screen from a total of 27×100-plate SLAM experiments. 800 wells demonstrated neutralisation in the HEK-blue assay. 170 wells had desirable Biacore profiles, i.e. bin 1 antibodies with off-rates <5×10-4 s-1. Variable region cloning from these 170 wells was attempted and 160 successfully yielded fluorescent foci. 100 wells generated heavy and light chain variable region gene pairs following reverse transcription (RT)-PCR. These V-region genes were cloned as mouse IgG1 full-length antibodies and re-expressed in a HEK-293 transient expression system. Sequence analysis revealed that there were 27 unique families of anti-human IL-13 antibody. These recombinant antibodies were then retested for their ability to block recombinant hIL-13 (*E. coli*-derived and mammalian-derived), recombinant variant hIL-13 (R130Q) (*E. coli*-derived), natural wild type and variant hIL-13 (human donor-derived) and cynomolgus IL-13 (mammalian-derived) in the cell-based assay. Recombinant antibodies were also tested for their ability to bind variant human IL-13 (R130Q) and cynomolgus IL-13 in the Biacore. Following this characterisation, 5 antibody families fulfilled our criteria, i.e. sub-100 pM antibody with minimal drop-off in potency and affinity for all human and cynomolgus IL-13 preparations.

Humanization of all 5 families was performed. Based on neutralisation potency, affinity and donor content in humanised grafts, humanised CA154_652 (see below) was selected for further progression.

1.1 Humanization

The humanised antibody exemplified herein (Ab652) was prepared by grafting the CDRs from the rat antibody V-regions (Seq ID NOs 7 and 15) (CDRs disclosed herein in sequences 1 to 6) onto human germline antibody V-region frameworks. Alignments of the rat antibody (donor) V-region sequences with the human germline antibody (acceptor) V-region sequences are shown in FIG. 12, together with the designed humanised sequence. The CDRs grafted from the donor to the acceptor sequence are as defined by Kabat (Kabat et al. Sequence of proteins of immunological interest (1987). Bethesda Md., National Institutes of Health, US), with the exception of CDR-H1 where the combined Chothia/Kabat definition is used (see Adair et al. (1991) Humanised antibodies WO 91/09967). Human V-region VH2 3-12-26 plus JH4 J-region (V BASE, vbase.mrc-cpe.cam.ac.uk/) was chosen as the acceptor for the heavy chain CDRs. The heavy chain framework residues are all from the human germline gene, with the exception of residues 49 and 71 (Kabat numbering), where the donor residues Glycine (G49) and Arginine (R71) were retained, respectively. Retention of these two donor residues was essential for full activity of the humanised antibody. Human V-region VK1 2-1-(1) 02 plus JK4 J-region (V BASE, vbase.mrc-cpe.cam.ac.uk/) was chosen as the acceptor for the light chain CDRs. The light chain framework residues are all from the human germline gene.

Genes encoding initial V-region sequences were designed and constructed by an automated synthesis approach by Entelechon GmbH. A number of different variants of the heavy chain were created by modifying the VH gene by oligonucleotide-directed mutagenesis. The gL1 gene sequence was cloned into the UCB-Celltech human light chain expression vector pKH10.1, which contains DNA encoding the human Kappa chain constant region (Km3 allotype)—see SEQ ID No: 26 and SEQ ID NO:30. The eight grafted VH genes (gH1 to gH8) were cloned into the UCB-Celltech human gamma-4 heavy chain expression vector pVhγ4P FL, which contains DNA encoding the human gamma-4 heavy chain constant region with the hinge stabilising mutation S241P (Angal et al., Mol Immunol. 1993, 30(1):105-8). The gH2 VH gene was selected as the optimum heavy chain graft for potency and biophysical characteristics (described herein below), and was then subcloned into the UCB-Celltech human gamma-1 Fab vector pVhγ1F3, which contains DNA encoding the human gamma-1 CH1 domain (G1m17 allotype) (SEQ ID NO:38). Co-transfection of the resulting heavy chain plasmid with the light chain plasmid, into CHO-L761h cells resulted in the expression of the humanised antibody in the required Fab format. This antibody is referred to herein as Ab652 (also referred to as Ab652 Fab).

To facilitate the generation of a stable cell line expressing antibody Ab652, a single plasmid containing DNA encoding both the heavy and light chain expression cassettes and a glutamine synthetase (GS) selection marker was generated. The GS gene allows for the selection of recombinant CHO cells by permitting growth in media supplemented with the GS inhibitor methionine sulphoximine (Bebbington et al., Biotechnol. 1992, 10(2): 169-175).

1.2 Binding Affinity Measurements

The BIAcore technology monitors the binding between biomolecules in real time and without the requirement for labelling. One of the interactants, termed the ligand, is either immobilised directly or captured on the immobilised surface while the other, termed the analyte, flows in solution over the captured surface. The sensor detects the change in mass on the sensor surface as the analyte binds to the ligand to form a complex on the surface. This corresponds to the association process. The dissociation of the analyte from the ligand is monitored when the analyte is replaced by buffer. In the affinity BIAcore assay, the ligand is Ab652 and the analyte is human IL-13.

1.3 Receptor Cross-Blocking Assay

The Biacore receptor cross-blocking assay requires the capture of anti IL-13 Fab followed by IL-13 (as the first analyte) flowed over the captured ligand to form a stable complex on the sensor surface. A second analyte (recombinant soluble IL-13 receptor) is then flowed over this stable complex. The amount of binding of the second analyte to the stable complex is monitored. Anti IL-13 antibodies that do not allow the second analyte to bind to the stable antibody: IL-13 complex are classified as Site 1 competitors. Those anti IL-13 antibodies that allow the second analyte to bind to the stable antibody:IL-13 complex are classified as Site 2 competitors.

Materials

Instrument
  Biacore® 3000, Biacore AB, Uppsala, Sweden
Sensor Chip
  CM5 (research grade) Catalogue Number: BR-1001-14, Biacore AB, Uppsala, Sweden.
  Chips were stored at 4° C.
Amine Coupling Kit
  Catalogue Number: BR-1000-50, Biacore AB, Uppsala, Sweden.
  Ethyl-3-(3-dimethylaminopropyl) carbodiimide hydrochloride (EDC). Made up to 75 mg/mL in distilled water and stored in 200 µL aliquots at −70° C.
  N-Hydroxysuccinimide (NHS). Made up to 11.5 mg/mL in distilled water and stored in 200 µL aliquots at −70° C.
  1 M Ethanolamine hydrochloride-NaOH pH 8.5. Stored in 200 µL aliquots at −70° C.
Buffers
  Running buffer: HBS-EP (being 0.01 M HEPES pH 7.4, 0.15 M NaCl, 3 mM EDTA, 0.005% Surfactant P20). Catalogue Number: BR-1001-88, Biacore AB, Uppsala, Sweden. Buffer stored at 4° C.
  Immobilisation buffer: Acetate 5.0 (being 10 mM sodium acetate pH 5.0). Catalogue number: BR-1003-51, Biacore AB, Uppsala, Sweden. Buffer stored at 4° C.
Ligand Capture
  Affinipure F(ab')$_2$ fragment goat anti-human IgG, F(ab')$_2$ fragment specific. Jackson ImmunoResearch Inc (Pennsylvania, USA) Catalogue number: 109-006-097. Reagent stored at 4° C.
Ligand
  Ab652 (2.51, 21.7 and 3.86 mg/ml Fab), stored at 4° C.
  Anti-hIL-13 mIgG (R&D Systems Europe Ltd, Abingdon, Oxon. Catalogue number MAB-213, Lot number RL04).
Analytes
  Recombinant human IL-13 (0.2 mg/ml from D. Lightwood; R&D Systems Europe Ltd, Abingdon, Oxon. Catalogue number 213-IL-050), stored at −70° C. and thawed once for each assay.
  Recombinant human IL-13 receptor1 hFc (R&D Systems Europe Ltd, Abingdon, Oxon.
  Catalogue number 146-IL-100). Stored at −70° C. and thawed once for each assay.
  Recombinant human IL-13 receptor2 hFc (R&D Systems Europe Ltd, Abingdon, Oxon.
  Catalogue number 614-IL-100). Stored at −70° C. and thawed once for each assay.
Regeneration Solution
  40 mM HCl prepared by dilution with distilled water from an 11.6 M stock solution (BDH, Poole, England. Catalogue number: 101254H).
  5 mM NaOH prepared by dilution with distilled water from a 50 mM stock solution.
  Catalogue number: BR-1003-58, Biacore AB, Uppsala, Sweden.
Key Equipment
  Biacore 3000 Biosensor, GE Healthcare Ltd, Amersham Place, Little Chalfont, Buckinghamshire, HP7 9 NA. The instrument is maintained according to the manufacturers protocols.

1.4 Ab652 Binding Affinity Measurements

The assay format was capture of the Ab652 by immobilised anti-human F(ab')$_2$ then titration of the human hIL-13 over the captured surface.

BIA (Biamolecular Interaction Analysis) was performed using a BIAcore 3000 (BIAcore AB). Affinipure F(ab')$_2$ Fragment, goat anti-human IgG, F(ab')$_2$ fragment specific (Jackson ImmunoResearch) was immobilised on a CM5 Sensor Chip via amine coupling chemistry to a capture level of ≈4000 response units (RUs). A blank surface was prepared in a similar way, omitting the F(ab')$_2$ fragment from the procedure. HBS-EP buffer (10 mM HEPES pH 7.4, 0.15 M NaCl, 3 mM EDTA, 0.005% Surfactant P20, BIAcore AB) was used as the running buffer with a flow rate of 10 µL/min. A 10 µl injection of Ab652 Fab at ~0.2 µg/mL was used for capture by the immobilised anti-human IgG-F(ab')$_2$ to allow sufficient IL-13 binding but also to minimise mass transport limited binding effects. Human IL13 was titrated over the captured Ab652 at various concentrations (10 nM to 0.31 nM) at a flow rate of 30 µL/min. The surface was regenerated by a 10 µL injection of 40 mM HCl, followed by a 5 µL injection of 5 mM NaOH at a flowrate of 10 µL/min.

Background subtraction binding curves were analysed using the BIAevaluation software (version 3.2) following standard procedures. Kinetic parameters were determined from the fitting algorithm.

TABLE 1

| sample | ka (1/Ms) | kd (1/s) | KD | KD pM |
|---|---|---|---|---|
| Ab652 average of 3 determinations | 4.51E+06 | 6.52E−05 | 1.52E−11 | 15 |

1.5 IL-13 Receptor Cross-Blocking Studies

The BIAcore receptor cross-blocking assay requires the capture of anti-IL-13 Fab followed by IL-13 (as the first analyte) flowed over the capture ligand to form a stable complex on the sensor surface. A second analyte (recombinant soluble IL-13 receptor) is then flowed over this stable complex. The amount of binding of the second analyte to the stable complex is then monitored. Anti-IL-13 antibodies that do not allow the second analyte to bind to the stable antibody:IL-13 complex are classified as Axis 1 competitors. Those anti IL-13 antibodies that allow the second analyte to bind the stable antibody:IL-13 complex are classified as Axis 2 competitors.

All experiments were performed using at Biacore 3000 biosensor at 25° C. HBS-EP buffer was used as the running buffer with a flow rate of 10 µL/minute (min) The same sensor surfaces were used as described for the affinity determinations.

A 10 µl injection of ~0.2 µg/ml of the anti human IL-13 Fab was used for capture by the goat F(ab')2 IgG, anti-human F(ab')2-fragment specific sensor surface. The anti human IL-13 Fab at 0.2 ug/ml gave sufficient anti-human IL-13 binding. Human IL-13 at 25 nM was injected over the captured antibody followed immediately by soluble human IL-13 receptor at 100 nM at a flow rate of 10 µL/min. The surface was regenerated by two 30 µL injections of 40 mM HCl, followed by a 5 µL injection of 5 mM NaOH at a flow rate of 30 µL/min Background subtracted binding curves were analysed using the BIAevaluation software provided by the manufacturer (version 3.2) following standard procedures.

TABLE 2

Biacore Blocking Summary

| Antibody | Ab binding | hIL-13 binding | hIL-13Ra1 binding | hIL-13Ra2 binding |
|---|---|---|---|---|
| Ab652 | 103.1 | 22.4 | — | 1.5 |
| Ab652 | 72.6 | 18.5 | −0.4 | — |
| Control Antibody | 138.4 | 13.9 | — | 51.4 |
| Control Antibody | 126 | 11.6 | 15.4 | — |

IL-13 interacts with either of two receptors (IL-13Rα1 and IL-13Rα2) to form a complex. Only the hIL-13/hIL-13 α1 complex signals. Therefore, anti-IL13 antibodies that inhibit IL-13 dependent signalling can mediate this effect by blocking the interaction with hIL-13 al. The site of interaction of Ab652 on human IL-13 was to be determined in a BIAcore assay. Ab652 was captured by an immobilised anti-human F(ab')$_2$ surface and then hIL-13 was in turn captured by the Ab652. The binding of the soluble IL-13 Rα1 to the captured IL-13/antibody complex was assessed. The assay was repeated with hIL-13Rα2 substituted for hIL-13Rα1. IL-13 presented by Ab652 could not bind either of the IL-13 receptors, but a commercial control anti-IL-13 antibody (mAb 213) was capable of presenting IL-13 to the soluble IL-13 receptor. In conclusion, Ab652 inhibits IL-13 binding to both the hIL-13 receptor subunits, defining it as an Axis 1 competitor.

TABLE 3

Affinity of purified Ab652 Fab for hIL-13

| | Ka (1/Ms) | kd (1/s) (on rate) | KD (off rate) | KD pM (affinity measured KD) |
|---|---|---|---|---|
| Ab652 | 4.83E+06 | 4.22E−05 | 8.73E−12 | 9 |
| Ab652 | 5.09E+06 | 6.64E−05 | 1.30E−11 | 13 |
| | 4.97E+06 | 5.90E−05 | 1.19E−11 | 12 |
| | 5.60E+06 | 6.70E−05 | 1.20E−11 | 12 |
| | 4.45E+06 | 7.11E−05 | 1.60E−11 | 16 |
| | 5.11E+06 | 4.67E−05 | 9.14E−12 | 9 |
| | 4.87E+06 | 6.25E−05 | 1.28E−11 | 13 |
| Ab652 | 3.61E+06 | 8.69E−05 | 2.40E−11 | 24 |
| AVERAGE | 4.82E+06 | 6.27E−05 | 1.34E−11 | 13 |
| SD | 5.84E+05 | 1.4E−05 | 4.84E−12 | |

The affinity of Ab652 for hIL-13 was determined in a Biacore assay over three separate assays. The affinity was in the range 9-24 pM with a mean of 13.4 (+4.8) pM 1.6 Cell-Based Potency The in vitro potency of Ab652 Fab to neutralize IL-13 was investigated using the HEK-BLUE™ STAT-6 assay (Invivogen). The assay comprises HEK293 cells stably expressing human STAT-6 and stably expressing secreted embryonic alkaline phosphatase (SEAP) under the control of the IFN-β minimal promoter fused to four STAT-6 binding sites. The neutralisation potency (IC$_{50}$) of Ab652 was assessed using different types of human IL-13, used in the assay at 250 pg/mL. Neutralisation potency was assessed against recombinant wild-type human IL-13 produced from bacterial (E. coli) and mammalian (rat fibroblasts) host cells. Neutralisation potency was assessed against natural wild-type and variant R130Q human IL-13 produced from human T-lymphocytes and against recombinant cynomolgus monkey IL-13 produced in mammalian cells. R130Q hIL-13 was not purified and the concentration was determined by hIL-13

ELISA. Cynomolgus IL-13 was not purified and was used at a concentration giving an equivalent response in the assay as 250 pg/mL hIL-13. In addition, the neutralisation potency of CA154_652.g2 Fab was measured following nebulisation using the PARE MAW® mesh nebuliser. Table 4: $IC_{50}$ values of Ab652 Fab against multiple forms of IL-13 in the HEK Blue Assay. For determination of functional affinity IL-13 titrations were performed in the presence of fixed concentrations of Ab652. Schild-plot analysis was applied to data to determine $K_D$ values for neutralisation of recombinant human wild-type IL-13 and recombinant cynomolgus monkey IL-13. Table 5: $IC_{50}$ and $K_D$ values of Ab652 Fab against multiple forms of IL-13 in the HEK Blue Assay.

TABLE 4

| IL-13 source (250 pg/ml) | $IC_{50}$ Ab652 Fab (ng/ml) |
|---|---|
| *E. coli*-derived, wild type | 1.05 |
| Mammalian (rat fibroblasts), wild type | 0.57 |
| Natural human T cell, wild type | 2.12 |
| Natural human T cell, R130Q variant | 1.66 |
| Cynomolgus on human receptor (1/4,000 = 250 pg/ml) | 1.61 |
| Nebulised Fab | 1.15 |

TABLE 5

| | | $IC_{50}$ ± SEM of Ab652 | | Functional Affinity $K_D$ of Ab652 | |
|---|---|---|---|---|---|
| | Source of IL-13 | ng/ml | pM | ng/ml | pM |
| Potency against Wild-Type Human IL-13 | Recombinant, *E. coli* derived (purified) | 0.670 ± 0.235 (n = 4) | 14.267 ± 4.943 (n = 4) | — | — |
| | Recombinant, mammalian cell derived (transfected Rat Fibroblast or HEK293 supernatant) | 0.611 ± 0.039 (n = 2) | 12.857 ± 0.821 (n = 2) | 0.103 (n = 1) | 2.173 (n = 1) |
| | Natural, Homozygous wild-type Donor derived (PBMC supernatant) | 1.544 ± 0.140 (n = 9) | 32.503 ± 2.949 (n = 9) | — | — |
| Potency against variant Human IL-13 | Natural, Homozygous R130Q variant Donor derived (PBMC supernatant) | 0.861 ± 0.141 (n = 7) | 20.079 ± 3.082 (n = 7) | — | — |
| Potency against Cynomolgus IL-13 | Recombinant, mammalian cell derived (transfected Rat Fibroblast or HEK293 supernatant) | 3.342 ± 0.431 (n = 13) | 70.328 ± 9.072 (n = 13) | 0.210 (n = 1) | 4.414 (n = 1) |
| Potency against Rat IL-13 | Recombinant, mammalian cell derived (transfected HEK293 supernatant) | 952.600 (n = 1) | 20,046.300 (n = 1) | — | — |
| Potency against Dog IL-13 | Recombinant, mammalian cell derived (transfected HEK293 supernatant) | Not cross-reactive (n = 2) | Not cross-reactive (n = 2) | — | — |

Overall, these data demonstrate that Ab652 Fab is similarly potent at neutralizing recombinant and natural human IL-13 produced from bacterial and mammalian sources. The potency of CA154_652.g2 against cynomolgus IL-13 in this assay is no more than 3-fold lower than against human IL-13 also generated from rat fibroblasts. The potency of CA154_652.g2 is not altered following nebulisation using the PARI eFLOW® nebuliser.

1.7 Physical Characterisation of Ab652

As described above 8 different antibody grafted variable regions were generated using the CDRs derived from the selected rat antibody (SEQ ID NOs: 1-6, FIG. 1). Selection of Ab652 (gL1gH2) from those 8 grafts was based on potency as described above and biophysical characteristics.

Based on the data generated for all the grafted variable regions tested, antibody 652 was chosen because it:

Maintained the highest affinity against hIL-13 and variant IL-13

Had the highest melting temperature, Tm (indicator of greater stability)

Greatest pH stability (by Circular Dichroism) i.e. showed less disturbance at low pH No aggregation on shaking or when nebulised In contrast, some of the other grafts tested showed a reduction in binding affinity, poor pH stability and aggregation by shaking and/or nebulisation.

1.7.1 Effect of Nebulisation

To determine whether Ab652 was suitable for nebulisation the PARI eFLOW® nebuliser was used. Volumes of 2.5 mL of Ab652 solution in 50 mM sodium acetate/125 mM sodium chloride pH5 were nebulised at ambient temperature (about 21° C.) and collected by condensing the nebulisate in cooled collection tubes. Subsequent analysis indicated no apparent degradation. The study was also repeated using a solution in PBS, pH 7. A positive control of IgG4 was included, having been found to aggregate during nebulisation. Analysis of the nebulised samples was by size exclusion, SDS-PAGE, dynamic light scattering and ligand binding, with the particular aim of detecting aggregated material present. No change was apparent by any of those techniques indicating that Ab652 was resistant to damage during nebulisation.

1.7.2 Summary of the Physical Characteristics of Ab652 pI (isoelectric point) 8 (average of two determinations)

Thermal stability Tm 84° C.

No aggregation of Ab652 was observed when the antibody was subjected to agitation/shaking or nebulisation 2. Effect of Ab652 in a Non-Human Primate Model of Asthma Objective The objective of this study was to evaluate the efficacy of Ab652 in a non-human primate model of asthma. Primary endpoints included the effects on bronchoalveolar lavage (BAL) cell counts, chemokine levels, and early and late pulmonary function changes as assessed by lung resistance ($R_L$).

Methods

Ab652 was delivered using a mesh nebuliser. Breath simulation studies were conducted using typical ventilator parameters and tubing set-up used at the study facility. The results of the breath simulation studies indicated that 40.4% of the material charge in the nebuliser would be delivered at the level of the endotracheal tube.

Study animals were selected on the basis of historical pulmonary function values and BAL eosinophil counts. In the screening session, animals underwent *Ascaris suum* (*A. suum*) antigen challenge before assignment to treatment groups in order to characterize their normal (untreated) response to *A. suum*. After this screening session, animals were assigned to dose groups on the basis of BAL cell counts and pulmonary function data from the screening session. In the treatment session, animals received either nebulised vehicle (PBS), or nebulised Ab652 at dose level in the nebuliser of either 0.1, 1, 10, and 60 mg/animal/day. Doses were administered via nebuliser on Days −2, −1, 1, 2, and 3. On Days 1 and 2, treatment administration occurred approximately 30 minutes before *A. suum* challenge.

Challenge procedures were identical for both sessions. Each animal was challenged on Days 1 and 2, and pulmonary function values ($R_L$) were recorded for at least 15 minutes after each antigen challenge and at 24 h after each allergen challenge. BAL fluid was collected before the first challenge and approximately 24 h after the second challenge for evaluation of total cell numbers, morphology, and differential counts in order to assess the degree of pulmonary inflammation. Samples of BAL supernatant were collected and analysed for determination of chemokine concentration.

Results

Nebulised Ab652 significantly inhibited the increase in BAL eotaxin-3 at low mg/day doses (FIG. 13). Nebulised Ab652 caused a dose-dependent inhibition of the increase in BAL eosinophils measured between the screening and treatment sessions (FIG. 14). Nebulised Ab652 significantly and dose-dependently inhibited the peak early phase response on day 2 measured up to 15 minutes following *Ascaris* challenge in the treatment session (FIG. 15). Nebulised Ab652 significantly and dose-dependently inhibited the late phase response measured 24 hours after day 2 allergen challenge (FIG. 16).

CONCLUSIONS

The data generated with nebulised Ab652 in the *Ascaris* model of asthma in cynomolgus monkeys demonstrate that IL-13-driven allergic lung inflammation is sensitive to pharmacological modulation by a neutralising anti-IL-13 Fab fragment delivered directly to the airways in an aerosol. Significantly Ab652 was potent, demonstrating efficacy at low mg/day doses.

It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

SEQUENCE LISTING

```
<160> NUMBER OF SEQ ID NOS: 46

<210> SEQ ID NO 1
<211> LENGTH: 10
<212> TYPE: PRT
<213> ORGANISM: Artificial
<220> FEATURE:
<223> OTHER INFORMATION: CDRH1

<400> SEQUENCE: 1

Gly Phe Ser Leu Thr Asn Tyr His Val Gln
1               5                   10

<210> SEQ ID NO 2
<211> LENGTH: 16
<212> TYPE: PRT
<213> ORGANISM: Artificial
<220> FEATURE:
<223> OTHER INFORMATION: CDRH2

<400> SEQUENCE: 2

Val Met Trp Ser Asp Gly Asp Thr Ser Phe Asn Ser Val Leu Lys Ser
1               5                   10                  15
```

```
<210> SEQ ID NO 3
<211> LENGTH: 12
<212> TYPE: PRT
<213> ORGANISM: Artificial
<220> FEATURE:
<223> OTHER INFORMATION: CDRH3

<400> SEQUENCE: 3

Asp Gly Thr Ile Ala Ala Met Asp Tyr Phe Asp Tyr
1               5                   10

<210> SEQ ID NO 4
<211> LENGTH: 11
<212> TYPE: PRT
<213> ORGANISM: Artificial
<220> FEATURE:
<223> OTHER INFORMATION: CDRL1

<400> SEQUENCE: 4

Leu Ala Ser Glu Asp Ile Ser Asn Tyr Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: CDRL2

<400> SEQUENCE: 5

His Thr Ser Arg Leu Gln Asp
1               5

<210> SEQ ID NO 6
<211> LENGTH: 9
<212> TYPE: PRT
<213> ORGANISM: Artificial
<220> FEATURE:
<223> OTHER INFORMATION: CDRL3

<400> SEQUENCE: 6

Gln Gln Gly Tyr Arg Phe Pro Leu Thr
1               5

<210> SEQ ID NO 7
<211> LENGTH: 107
<212> TYPE: PRT
<213> ORGANISM: Artificial
<220> FEATURE:
<223> OTHER INFORMATION: Rat Variable Light Chain

<400> SEQUENCE: 7

Asp Ile Gln Met Thr Gln Ser Pro His Ser Leu Ser Ala Ser Leu Gly
1               5                   10                  15

Glu Thr Val Ser Ile Glu Cys Leu Ala Ser Glu Asp Ile Ser Asn Tyr
            20                  25                  30

Leu Ala Trp Tyr Gln Gln Lys Pro Gly Lys Ser Pro Gln Leu Leu Ile
        35                  40                  45

Tyr His Thr Ser Arg Leu Gln Asp Gly Val Pro Ser Arg Phe Ser Gly
    50                  55                  60

Ser Gly Ser Gly Thr Gln Phe Ser Leu Lys Ile Ser Asn Met Gln Pro
65                  70                  75                  80

Glu Asp Glu Gly Val Tyr Tyr Cys Gln Gln Gly Tyr Arg Phe Pro Leu
```

```
                    85                  90                  95
Thr Phe Gly Ser Gly Thr Lys Leu Glu Leu Lys
                100                 105

<210> SEQ ID NO 8
<211> LENGTH: 321
<212> TYPE: DNA
<213> ORGANISM: Artificial
<220> FEATURE:
<223> OTHER INFORMATION: Rat Variable Light Chain

<400> SEQUENCE: 8
gacatccaga tgacacagtc tccacattcc ctgtctgcat ctctgggaga aactgtctcc    60
atcgaatgtc tagcaagtga ggacatttcc aattatttag cgtggtatca gcagaagcca   120
ggaaaatctc ctcagctctt gatctatcat acaagtaggt tgcaagatgg ggtcccatca   180
cggttcagtg gcagtggatc tggcacacag ttttctctca agatcagtaa catgcaacct   240
gaagatgaag gggtctatta ctgtcaacag ggttacaggt ttccgctcac gttcggttct   300
gggaccaagc tggaattgaa a                                             321

<210> SEQ ID NO 9
<211> LENGTH: 127
<212> TYPE: PRT
<213> ORGANISM: Artificial
<220> FEATURE:
<223> OTHER INFORMATION: Rat Variable Light Chain with signal sequence

<400> SEQUENCE: 9

Met Gly Val Pro Thr Gln Leu Leu Gly Leu Leu Leu Leu Trp Ile Thr
 1               5                  10                  15

Asp Ala Ile Cys Asp Ile Gln Met Thr Gln Ser Pro His Ser Leu Ser
                20                  25                  30

Ala Ser Leu Gly Glu Thr Val Ser Ile Glu Cys Leu Ala Ser Glu Asp
            35                  40                  45

Ile Ser Asn Tyr Leu Ala Trp Tyr Gln Gln Lys Pro Gly Lys Ser Pro
        50                  55                  60

Gln Leu Leu Ile Tyr His Thr Ser Arg Leu Gln Asp Gly Val Pro Ser
 65                 70                  75                  80

Arg Phe Ser Gly Ser Gly Ser Gly Thr Gln Phe Ser Leu Lys Ile Ser
                85                  90                  95

Asn Met Gln Pro Glu Asp Glu Gly Val Tyr Tyr Cys Gln Gln Gly Tyr
                100                 105                 110

Arg Phe Pro Leu Thr Phe Gly Ser Gly Thr Lys Leu Glu Leu Lys
            115                 120                 125

<210> SEQ ID NO 10
<211> LENGTH: 381
<212> TYPE: DNA
<213> ORGANISM: Artificial
<220> FEATURE:
<223> OTHER INFORMATION: Rat Variable Light Chain with signal sequence

<400> SEQUENCE: 10
atgggtgtcc ccactcagct cttggggttg ttgttactgt ggattacaga tgccatatgt    60
gacatccaga tgacacagtc tccacattcc ctgtctgcat ctctgggaga aactgtctcc   120
atcgaatgtc tagcaagtga ggacatttcc aattatttag cgtggtatca gcagaagcca   180
ggaaaatctc ctcagctctt gatctatcat acaagtaggt tgcaagatgg ggtcccatca   240
```

```
cggttcagtg gcagtggatc tggcacacag ttttctctca agatcagtaa catgcaacct    300
gaagatgaag gggtctatta ctgtcaacag ggttacaggt ttccgctcac gttcggttct    360
gggaccaagc tggaattgaa a                                              381
```

<210> SEQ ID NO 11
<211> LENGTH: 214
<212> TYPE: PRT
<213> ORGANISM: Artificial
<220> FEATURE:
<223> OTHER INFORMATION: Rat Light chain

<400> SEQUENCE: 11

```
Asp Ile Gln Met Thr Gln Ser Pro His Ser Leu Ser Ala Ser Leu Gly
1               5                   10                  15

Glu Thr Val Ser Ile Glu Cys Leu Ala Ser Glu Asp Ile Ser Asn Tyr
            20                  25                  30

Leu Ala Trp Tyr Gln Gln Lys Pro Gly Lys Ser Pro Gln Leu Leu Ile
        35                  40                  45

Tyr His Thr Ser Arg Leu Gln Asp Gly Val Pro Ser Arg Phe Ser Gly
    50                  55                  60

Ser Gly Ser Gly Thr Gln Phe Ser Leu Lys Ile Ser Asn Met Gln Pro
65                  70                  75                  80

Glu Asp Glu Gly Val Tyr Tyr Cys Gln Gln Gly Tyr Arg Phe Pro Leu
                85                  90                  95

Thr Phe Gly Ser Gly Thr Lys Leu Glu Leu Lys Arg Ala Asp Ala Ala
            100                 105                 110

Pro Thr Val Ser Ile Phe Pro Pro Ser Thr Glu Gln Leu Ala Thr Gly
        115                 120                 125

Gly Ala Ser Val Val Cys Leu Met Asn Asn Phe Tyr Pro Arg Asp Ile
    130                 135                 140

Ser Val Lys Trp Lys Ile Asp Gly Thr Glu Arg Arg Asp Gly Val Leu
145                 150                 155                 160

Asp Ser Val Thr Asp Gln Asp Ser Lys Asp Ser Thr Tyr Ser Met Ser
                165                 170                 175

Ser Thr Leu Ser Leu Thr Lys Ala Asp Tyr Glu Ser His Asn Leu Tyr
            180                 185                 190

Thr Cys Glu Val Val His Lys Thr Ser Ser Ser Pro Val Val Lys Ser
        195                 200                 205

Phe Asn Arg Asn Glu Cys
    210
```

<210> SEQ ID NO 12
<211> LENGTH: 642
<212> TYPE: DNA
<213> ORGANISM: Artificial
<220> FEATURE:
<223> OTHER INFORMATION: Rat Light chain

<400> SEQUENCE: 12

```
gacatccaga tgacacagtc tccacattcc ctgtctgcat ctctgggaga aactgtctcc    60
atcgaatgtc tagcaagtga ggacatttcc aattatttag cgtggtatca gcagaagcca    120
ggaaaatctc ctcagctctt gatctatcat acaagtaggt tgcaagatgg ggtcccatca    180
cggttcagtg gcagtggatc tggcacacag ttttctctca agatcagtaa catgcaacct    240
gaagatgaag gggtctatta ctgtcaacag ggttacaggt ttccgctcac gttcggttct    300
gggaccaagc tggaattgaa acgggctgat gctgcaccaa ctgtatctat cttcccacca    360
```

```
tccacggaac agttagcaac tggaggtgcc tcagtcgtgt gcctcatgaa caacttctat    420
cccagagaca tcagtgtcaa gtggaagatt gatggcactg aacgacgaga tggtgtcctg    480
gacagtgtta ctgatcagga cagcaaagac agcacgtaca gcatgagcag caccctctcg    540
ttgaccaagg ctgactatga aagtcataac ctctatacct gtgaggttgt tcataagaca    600
tcatcctcac ccgtcgtcaa gagcttcaac aggaatgagt gt                      642
```

<210> SEQ ID NO 13
<211> LENGTH: 234
<212> TYPE: PRT
<213> ORGANISM: Artificial
<220> FEATURE:
<223> OTHER INFORMATION: Rat Light chain with signal sequence

<400> SEQUENCE: 13

```
Met Gly Val Pro Thr Gln Leu Leu Gly Leu Leu Leu Trp Ile Thr
1               5                   10                  15

Asp Ala Ile Cys Asp Ile Gln Met Thr Gln Ser Pro His Ser Leu Ser
            20                  25                  30

Ala Ser Leu Gly Glu Thr Val Ser Ile Glu Cys Leu Ala Ser Glu Asp
        35                  40                  45

Ile Ser Asn Tyr Leu Ala Trp Tyr Gln Gln Lys Pro Gly Lys Ser Pro
    50                  55                  60

Gln Leu Leu Ile Tyr His Thr Ser Arg Leu Gln Asp Gly Val Pro Ser
65                  70                  75                  80

Arg Phe Ser Gly Ser Gly Ser Gly Thr Gln Phe Ser Leu Lys Ile Ser
                85                  90                  95

Asn Met Gln Pro Glu Asp Glu Gly Val Tyr Tyr Cys Gln Gln Gly Tyr
            100                 105                 110

Arg Phe Pro Leu Thr Phe Gly Ser Gly Thr Lys Leu Glu Leu Lys Arg
        115                 120                 125

Ala Asp Ala Ala Pro Thr Val Ser Ile Phe Pro Pro Ser Thr Glu Gln
    130                 135                 140

Leu Ala Thr Gly Gly Ala Ser Val Val Cys Leu Met Asn Asn Phe Tyr
145                 150                 155                 160

Pro Arg Asp Ile Ser Val Lys Trp Lys Ile Asp Gly Thr Glu Arg Arg
                165                 170                 175

Asp Gly Val Leu Asp Ser Val Thr Asp Gln Asp Ser Lys Asp Ser Thr
            180                 185                 190

Tyr Ser Met Ser Ser Thr Leu Ser Leu Thr Lys Ala Asp Tyr Glu Ser
        195                 200                 205

His Asn Leu Tyr Thr Cys Glu Val Val His Lys Thr Ser Ser Ser Pro
    210                 215                 220

Val Val Lys Ser Phe Asn Arg Asn Glu Cys
225                 230
```

<210> SEQ ID NO 14
<211> LENGTH: 702
<212> TYPE: DNA
<213> ORGANISM: Artificial
<220> FEATURE:
<223> OTHER INFORMATION: Rat Light chain with signal sequence

<400> SEQUENCE: 14

```
atgggtgtcc ccactcagct cttggggttg ttgttactgt ggattacaga tgccatatgt     60
gacatccaga tgacacagtc tccacattcc ctgtctgcat ctctgggaga aactgtctcc    120
```

```
atcgaatgtc tagcaagtga ggacatttcc aattatttag cgtggtatca gcagaagcca    180
ggaaaatctc ctcagctctt gatctatcat acaagtaggt tgcaagatgg ggtcccatca    240
cggttcagtg gcagtggatc tggcacacag ttttctctca agatcagtaa catgcaacct    300
gaagatgaag gggtctatta ctgtcaacag ggttacaggt ttccgctcac gttcggttct    360
gggaccaagc tggaattgaa acgggctgat gctgcaccaa ctgtatctat cttcccacca    420
tccacggaac agttagcaac tggaggtgcc tcagtcgtgt gcctcatgaa caacttctat    480
cccagagaca tcagtgtcaa gtggaagatt gatggcactg aacgacgaga tggtgtcctg    540
gacagtgtta ctgatcagga cagcaaagac agcacgtaca gcatgagcag caccctctcg    600
ttgaccaagg ctgactatga aagtcataac ctctatacct gtgaggttgt tcataagaca    660
tcatcctcac ccgtcgtcaa gagcttcaac aggaatgagt gt                       702
```

<210> SEQ ID NO 15
<211> LENGTH: 119
<212> TYPE: PRT
<213> ORGANISM: Artificial
<220> FEATURE:
<223> OTHER INFORMATION: Rat variable heavy chain

<400> SEQUENCE: 15

```
Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Tyr
            20                  25                  30

His Val Gln Trp Val Arg Gln Pro Pro Gly Lys Gly Leu Glu Trp Met
        35                  40                  45

Gly Val Met Trp Ser Asp Gly Asp Thr Ser Phe Asn Ser Val Leu Lys
    50                  55                  60

Ser Arg Leu Ser Ile Ser Arg Asp Thr Ser Lys Ser Gln Val Phe Leu
65                  70                  75                  80

Lys Met Ser Ser Leu Gln Thr Glu Asp Thr Ala Thr Tyr Tyr Cys Ala
                85                  90                  95

Arg Asp Gly Thr Ile Ala Ala Met Asp Tyr Phe Asp Tyr Trp Gly Gln
            100                 105                 110

Gly Val Met Val Thr Val Ser
        115
```

<210> SEQ ID NO 16
<211> LENGTH: 357
<212> TYPE: DNA
<213> ORGANISM: Artificial
<220> FEATURE:
<223> OTHER INFORMATION: Rat variable heavy chain

<400> SEQUENCE: 16

```
caggtgcagc tgaaggagtc aggacctggc ctggtgcagc cctcacagac cctgtctctc     60
acctgcactg tctctgggtt ctcattaacc aactatcatg tgcagtgggt tcggcagcct    120
ccaggaaaag gtctggagtg gatgggagta atgtggagtg atggagacac atcatttaat    180
tcagttctca aatctcgact gagcatcagc aggacacctc caagagcca gttttctta     240 aaaatgagca gtctgcaaac tgaagacaca gccacttact actgtgccag agatggaact    300
atagcagcta tggactactt tgattattgg ggccaaggag tcatggtcac cgtctcg      357
```

<210> SEQ ID NO 17

```
<211> LENGTH: 138
<212> TYPE: PRT
<213> ORGANISM: Artificial
<220> FEATURE:
<223> OTHER INFORMATION: Rat variable heavy chain with signal sequence

<400> SEQUENCE: 17

Met Ala Val Leu Val Leu Leu Leu Cys Leu Met Thr Phe Pro Ser Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Asn Tyr His Val Gln Trp Val Arg Gln Pro Pro Gly Lys Gly Leu
    50                  55                  60

Glu Trp Met Gly Val Met Trp Ser Asp Gly Asp Thr Ser Phe Asn Ser
65                  70                  75                  80

Val Leu Lys Ser Arg Leu Ser Ile Ser Arg Asp Thr Ser Lys Ser Gln
                85                  90                  95

Val Phe Leu Lys Met Ser Ser Leu Gln Thr Glu Asp Thr Ala Thr Tyr
            100                 105                 110

Tyr Cys Ala Arg Asp Gly Thr Ile Ala Ala Met Asp Tyr Phe Asp Tyr
        115                 120                 125

Trp Gly Gln Gly Val Met Val Thr Val Ser
    130                 135

<210> SEQ ID NO 18
<211> LENGTH: 414
<212> TYPE: DNA
<213> ORGANISM: Artificial
<220> FEATURE:
<223> OTHER INFORMATION: Rat variable heavy chain with signal sequence

<400> SEQUENCE: 18
atggctgtcc tggtgctgtt gctctgcctg atgacatttc caagctgtgt cctgtcccag      60
gtgcagctga aggagtcagg acctggcctg gtgcagccct cacagaccct gtctctcacc     120
tgcactgtct ctgggttctc attaaccaac tatcatgtgc agtgggttcg gcagcctcca     180
ggaaaaggtc tggagtggat gggagtaatg tggagtgatg gagacacatc atttaattca     240
gttctcaaat ctcgactgag catcagcagg gacacctcca agagccaagt tttcttaaaa     300
atgagcagtc tgcaaactga agacacagcc acttactact gtgccagaga tggaactata     360
gcagctatgg actactttga ttattggggc caaggagtca tggtcaccgt ctcg           414

<210> SEQ ID NO 19
<211> LENGTH: 446
<212> TYPE: PRT
<213> ORGANISM: Artificial
<220> FEATURE:
<223> OTHER INFORMATION: Rat heavy chain

<400> SEQUENCE: 19

Gln Val Gln Leu Lys Glu Ser Gly Pro Gly Leu Val Gln Pro Ser Gln
1               5                   10                  15

Thr Leu Ser Leu Thr Cys Thr Val Ser Gly Phe Ser Leu Thr Asn Tyr
            20                  25                  30

His Val Gln Trp Val Arg Gln Pro Pro Gly Lys Gly Leu Glu Trp Met
        35                  40                  45

Gly Val Met Trp Ser Asp Gly Asp Thr Ser Phe Asn Ser Val Leu Lys
```

```
            50                  55                  60
Ser Arg Leu Ser Ile Ser Arg Asp Thr Ser Lys Ser Gln Val Phe Leu
 65                  70                  75                  80

Lys Met Ser Ser Leu Gln Thr Glu Asp Thr Ala Thr Tyr Tyr Cys Ala
                 85                  90                  95

Arg Asp Gly Thr Ile Ala Ala Met Asp Tyr Phe Asp Tyr Trp Gly Gln
                100                 105                 110

Gly Val Met Val Thr Val Ser Ser Ala Glu Thr Thr Ala Pro Ser Val
            115                 120                 125

Tyr Pro Leu Ala Pro Gly Thr Ala Leu Lys Ser Asn Ser Met Val Thr
130                 135                 140

Leu Gly Cys Leu Val Lys Gly Tyr Phe Pro Glu Pro Val Thr Val Thr
145                 150                 155                 160

Trp Asn Ser Gly Ala Leu Ser Ser Gly Val His Thr Phe Pro Ala Val
                165                 170                 175

Leu Gln Ser Gly Leu Tyr Thr Leu Thr Ser Ser Val Thr Val Pro Ser
            180                 185                 190

Ser Thr Trp Pro Ser Gln Thr Val Thr Cys Asn Val Ala His Pro Ala
            195                 200                 205

Ser Ser Thr Lys Val Asp Lys Lys Ile Val Pro Arg Asn Cys Gly Gly
210                 215                 220

Asp Cys Lys Pro Cys Ile Cys Thr Gly Ser Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Gln Asp Asp Pro Glu Val
            260                 265                 270

His Phe Ser Trp Phe Val Asp Asp Val Glu Val His Thr Ala Gln Thr
            275                 280                 285

Arg Pro Pro Glu Glu Gln Phe Asn Ser Thr Phe Arg Ser Val Ser Glu
290                 295                 300

Leu Pro Ile Leu His Gln Asp Trp Leu Asn Gly Arg Thr Phe Arg Cys
305                 310                 315                 320

Lys Val Thr Ser Ala Ala Phe Pro Ser Pro Ile Glu Lys Thr Ile Ser
                325                 330                 335

Lys Pro Glu Gly Arg Thr Gln Val Pro His Val Tyr Thr Met Ser Pro
            340                 345                 350

Thr Lys Glu Glu Met Thr Gln Asn Glu Val Ser Ile Thr Cys Met Val
            355                 360                 365

Lys Gly Phe Tyr Pro Pro Asp Ile Tyr Val Glu Trp Gln Met Asn Gly
370                 375                 380

Gln Pro Gln Glu Asn Tyr Lys Asn Thr Pro Pro Thr Met Asp Thr Asp
385                 390                 395                 400

Gly Ser Tyr Phe Leu Tyr Ser Lys Leu Asn Val Lys Lys Glu Lys Trp
                405                 410                 415

Gln Gln Gly Asn Thr Phe Thr Cys Ser Val Leu His Glu Gly Leu His
            420                 425                 430

Asn His His Thr Glu Lys Ser Leu Ser His Ser Pro Gly Lys
            435                 440                 445

<210> SEQ ID NO 20
<211> LENGTH: 1338
<212> TYPE: DNA
<213> ORGANISM: Artificial
```

<220> FEATURE:
<223> OTHER INFORMATION: Rat heavy chain

<400> SEQUENCE: 20

```
caggtgcagc tgaaggagtc aggacctggc ctggtgcagc cctcacagac cctgtctctc      60
acctgcactg tctctgggtt ctcattaacc aactatcatg tgcagtgggt tcggcagcct     120
ccaggaaaag gtctggagtg gatgggagta atgtggagtg atggagacac atcatttaat     180
tcagttctca aatctcgact gagcatcagc agggacacct ccaagagcca agttttctta     240
aaaatgagca gtctgcaaac tgaagacaca gccacttact actgtgccag agatggaact     300
atagcagcta tggactactt tgattattgg ggccaaggag tcatggtcac cgtctcgtca     360
gctgaaacaa cagccccatc tgtctatcca ctggctcctg aactgctctc aaaagtaac      420
tccatggtga ccctgggatg cctggtcaag ggctatttcc ctgagccagt caccgtgacc     480
tggaactctg gagccctgtc cagcggtgtg cacaccttcc agctgtcct gcagtctggg      540
ctctacactc tcaccagctc agtgactgta ccctccagca cctggcccag ccagaccgtc     600
acctgcaacg tagcccaccc ggccagcagc accaaggtgg acaagaaaat tgtgcccaga     660
aactgtggag tgattgcaa gccttgtata tgtacaggct cagaagtatc atctgtcttc      720
atcttccccc caaagcccaa agatgtgctc accatcactc tgactcctaa ggtcacgtgt     780
gttgtggtag acattagcca ggacgatccc gaggtccatt tcagctggtt tgtagatgac     840
gtggaagtcc acacagctca gactcgacca ccagaggagc agttcaacag cactttccgc     900
tcagtcagtg aactcccat cctgcaccag gactggctca atggcaggac gttcagatgc      960
aaggtcacca gtgcagcttt cccatccccc atcgagaaaa ccatctccaa acccgaaggc    1020
agaacacaag ttccgcatgt atacaccatg tcacctacca aggaagagat gacccagaat    1080
gaagtcagta tcacctgcat ggtaaaaggc ttctatcccc cagacattta tgtggagtgg    1140
cagatgaacg ggcagccaca ggaaaactac aagaacactc cacctacgat ggacacagat    1200
gggagttact tcctctacag caagctcaat gtgaagaagg aaaaatggca gcagggaaac    1260
acgttcacgt gttctgtgct gcatgaaggc ctgcacaacc accatactga aagagtctc     1320
tcccactctc cgggtaaa                                                  1338
```

<210> SEQ ID NO 21
<211> LENGTH: 465
<212> TYPE: PRT
<213> ORGANISM: Artificial
<220> FEATURE:
<223> OTHER INFORMATION: Rat heavy chain with signal sequence

<400> SEQUENCE: 21

```
Met Ala Val Leu Val Leu Leu Leu Cys Leu Met Thr Phe Pro Ser Cys
1               5                   10                  15

Val Leu Ser Gln Val Gln Leu Lys Glu Ser Gly Pro Gly Leu Val Gln
            20                  25                  30

Pro Ser Gln Thr Leu Ser Leu Thr Cys Thr Val Ser Gly Phe Ser Leu
        35                  40                  45

Thr Asn Tyr His Val Gln Trp Val Arg Gln Pro Pro Gly Lys Gly Leu
    50                  55                  60

Glu Trp Met Gly Val Met Trp Ser Asp Gly Asp Thr Ser Phe Asn Ser
65                  70                  75                  80

Val Leu Lys Ser Arg Leu Ser Ile Ser Arg Asp Thr Ser Lys Ser Gln
                85                  90                  95
```

Val Phe Leu Lys Met Ser Ser Leu Gln Thr Glu Asp Thr Ala Thr Tyr
            100                 105                 110

Tyr Cys Ala Arg Asp Gly Thr Ile Ala Ala Met Asp Tyr Phe Asp Tyr
            115                 120                 125

Trp Gly Gln Gly Val Met Val Thr Val Ser Ser Ala Glu Thr Thr Ala
        130                 135                 140

Pro Ser Val Tyr Pro Leu Ala Pro Gly Thr Ala Leu Lys Ser Asn Ser
145                 150                 155                 160

Met Val Thr Leu Gly Cys Leu Val Lys Gly Tyr Phe Pro Glu Pro Val
            165                 170                 175

Thr Val Thr Trp Asn Ser Gly Ala Leu Ser Ser Gly Val His Thr Phe
        180                 185                 190

Pro Ala Val Leu Gln Ser Gly Leu Tyr Thr Leu Thr Ser Ser Val Thr
        195                 200                 205

Val Pro Ser Ser Thr Trp Pro Ser Gln Thr Val Thr Cys Asn Val Ala
        210                 215                 220

His Pro Ala Ser Ser Thr Lys Val Asp Lys Lys Ile Val Pro Arg Asn
225                 230                 235                 240

Cys Gly Gly Asp Cys Lys Pro Cys Ile Cys Thr Gly Ser Glu Val Ser
            245                 250                 255

Ser Val Phe Ile Phe Pro Pro Lys Pro Lys Asp Val Leu Thr Ile Thr
            260                 265                 270

Leu Thr Pro Lys Val Thr Cys Val Val Val Asp Ile Ser Gln Asp Asp
        275                 280                 285

Pro Glu Val His Phe Ser Trp Phe Val Asp Asp Val Glu Val His Thr
        290                 295                 300

Ala Gln Thr Arg Pro Pro Glu Glu Gln Phe Asn Ser Thr Phe Arg Ser
305                 310                 315                 320

Val Ser Glu Leu Pro Ile Leu His Gln Asp Trp Leu Asn Gly Arg Thr
            325                 330                 335

Phe Arg Cys Lys Val Thr Ser Ala Ala Phe Pro Ser Pro Ile Glu Lys
            340                 345                 350

Thr Ile Ser Lys Pro Glu Gly Arg Thr Gln Val Pro His Val Tyr Thr
        355                 360                 365

Met Ser Pro Thr Lys Glu Glu Met Thr Gln Asn Glu Val Ser Ile Thr
        370                 375                 380

Cys Met Val Lys Gly Phe Tyr Pro Pro Asp Ile Tyr Val Glu Trp Gln
385                 390                 395                 400

Met Asn Gly Gln Pro Gln Glu Asn Tyr Lys Asn Thr Pro Pro Thr Met
            405                 410                 415

Asp Thr Asp Gly Ser Tyr Phe Leu Tyr Ser Lys Leu Asn Val Lys Lys
            420                 425                 430

Glu Lys Trp Gln Gln Gly Asn Thr Phe Thr Cys Ser Val Leu His Glu
        435                 440                 445

Gly Leu His Asn His His Thr Glu Lys Ser Leu Ser His Ser Pro Gly
        450                 455                 460

Lys
465

<210> SEQ ID NO 22
<211> LENGTH: 1395
<212> TYPE: DNA
<213> ORGANISM: Artificial
<220> FEATURE:
<223> OTHER INFORMATION: Rat heavy chain with signal sequence

<400> SEQUENCE: 22

```
atggctgtcc tggtgctgtt gctctgcctg atgacatttc caagctgtgt cctgtcccag      60
gtgcagctga aggagtcagg acctggcctg gtgcagccct cacagaccct gtctctcacc     120
tgcactgtct ctgggttctc attaaccaac tatcatgtgc agtgggttcg gcagcctcca     180
ggaaaaggtc tggagtggat gggagtaatg tggagtgatg agacacatc atttaattca      240
gttctcaaat ctcgactgag catcagcagg acacctcca agagccaagt tttcttaaaa      300
atgagcagtc tgcaaactga agacacagcc acttactact gtgccagaga tggaactata      360
gcagctatgg actactttga ttattgggc caaggagtca tggtcaccgt ctcgtcagct      420
gaaacaacag ccccatctgt ctatccactg gctcctggaa ctgctctcaa aagtaactcc      480
atggtgaccc tgggatgcct ggtcaagggc tatttccctg agccagtcac cgtgacctgg      540
aactctggag ccctgtccag cggtgtgcac accttccag ctgtcctgca gtctgggctc      600
tacactctca ccagctcagt gactgtaccc tccagcacct ggcccagcca gaccgtcacc      660
tgcaacgtag cccacccggc cagcagcacc aaggtggaca gaaaattgt gcccagaaac      720
tgtggaggtg attgcaagcc ttgtatatgt acaggctcag aagtatcatc tgtcttcatc      780
ttcccccaa agcccaaaga tgtgctcacc atcactctga ctcctaaggt cacgtgtgtt      840
gtggtagaca ttagccagga cgatcccgag gtccatttca ctggtttgt agatgacgtg      900
gaagtccaca cagctcagac tcgaccacca gaggagcagt tcaacagcac tttccgctca      960
gtcagtgaac tccccatcct gcaccaggac tggctcaatg caggacgtt cagatgcaag     1020
gtcaccagtg cagctttccc atcccccatc gagaaaacca tctccaaacc cgaaggcaga     1080
acacaagttc gcatgtata caccatgtca cctaccaagg aagagatgac ccagaatgaa     1140
gtcagtatca cctgcatggt aaaaggcttc tatccccag acatttatgt ggagtggcag     1200
atgaacgggc agccacagga aaactacaag aacactccac ctacgatgga cacagatggg     1260
agttacttcc tctacagcaa gctcaatgtg aagaaggaaa atggcagca gggaaacacg     1320
ttcacgtgtt ctgtgctgca tgaaggcctg cacaaccacc atactgagaa gagtctctcc     1380
cactctccgg gtaaa                                                      1395
```

<210> SEQ ID NO 23
<211> LENGTH: 107
<212> TYPE: PRT
<213> ORGANISM: Artificial
<220> FEATURE:
<223> OTHER INFORMATION: Ab652 VL

<400> SEQUENCE: 23

```
Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Ser Asn Tyr
            20                  25                  30

Leu Ala Trp Tyr Gln Gln Lys Pro Gly Lys Ala Pro Lys Leu Leu Ile
        35                  40                  45

Tyr His Thr Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Arg Phe Pro Leu
                85                  90                  95
```

Thr Phe Gly Gly Gly Thr Lys Val Glu Ile Lys
            100                 105

<210> SEQ ID NO 24
<211> LENGTH: 321
<212> TYPE: DNA
<213> ORGANISM: Artificial
<220> FEATURE:
<223> OTHER INFORMATION: Ab652 VL

<400> SEQUENCE: 24
gatatccaga tgacccagag tccaagcagt ctctccgcca gcgtaggcga tcgtgtgact    60
attacctgtc tggctagcga ggacatctcc aactacctgg cgtggtatca gcagaaaccg   120
ggtaaagcgc cgaaactgct gatctatcac acttcccgtc tgcaggacgg tgttccgtct   180
cgtttctctg gttccggttc tggtacggac ttcaccctga ccatctcttc tctgcagcca   240
gaagacttcg cgacttacta ctgccagcag ggttaccgtt ttccgctgac cttcggtggt   300
ggtaccaaag ttgaaatcaa a                                             321

<210> SEQ ID NO 25
<211> LENGTH: 127
<212> TYPE: PRT
<213> ORGANISM: Artificial
<220> FEATURE:
<223> OTHER INFORMATION: Ab652 VL with signal sequence

<400> SEQUENCE: 25

Met Ser Val Pro Thr Gln Val Leu Gly Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Ser Asn Tyr Leu Ala Trp Tyr Gln Gln Lys Pro Gly Lys Ala Pro
    50                  55                  60

Lys Leu Leu Ile Tyr His Thr Ser Arg Leu Gln Asp Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gly Tyr
            100                 105                 110

Arg Phe Pro Leu Thr Phe Gly Gly Gly Thr Lys Val Glu Ile Lys
        115                 120                 125

<210> SEQ ID NO 26
<211> LENGTH: 381
<212> TYPE: DNA
<213> ORGANISM: Artificial
<220> FEATURE:
<223> OTHER INFORMATION: Ab652 VL with signal sequence

<400> SEQUENCE: 26
atgtctgtcc ccacccaagt cctcggactc ctgctactct ggcttacaga tgccagatgc    60
gatatccaga tgacccagag tccaagcagt ctctccgcca gcgtaggcga tcgtgtgact   120
attacctgtc tggctagcga ggacatctcc aactacctgg cgtggtatca gcagaaaccg   180
ggtaaagcgc cgaaactgct gatctatcac acttcccgtc tgcaggacgg tgttccgtct   240
cgtttctctg gttccggttc tggtacggac ttcaccctga ccatctcttc tctgcagcca   300
gaagacttcg cgacttacta ctgccagcag ggttaccgtt ttccgctgac cttcggtggt    360
ggtaccaaag ttgaaatcaa a                                               381

<210> SEQ ID NO 27
<211> LENGTH: 214
<212> TYPE: PRT
<213> ORGANISM: Artificial
<220> FEATURE:
<223> OTHER INFORMATION: Ab652 light chain (variable and constant)

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Leu Ala Ser Glu Asp Ile Ser Asn Tyr
            20                  25                  30

Leu Ala Trp Tyr Gln Gln Lys Pro Gly Lys Ala Pro Lys Leu Leu Ile
        35                  40                  45

Tyr His Thr Ser Arg Leu Gln Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Arg Phe Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 28
<211> LENGTH: 642
<212> TYPE: DNA
<213> ORGANISM: Artificial
<220> FEATURE:
<223> OTHER INFORMATION: Ab652 light chain (variable and constant)

<400> SEQUENCE: 28
gatatccaga tgacccagag tccaagcagt ctctccgcca gcgtaggcga tcgtgtgact    60
attacctgtc tggctagcga ggacatctcc aactacctgg cgtggtatca gcagaaaccg   120
ggtaaagcgc cgaaactgct gatctatcac acttcccgtc tgcaggacgg tgttccgtct   180
cgtttctctg gttccggttc tggtacggac ttcaccctga ccatctcttc tctgcagcca   240
gaagacttcg cgacttacta ctgccagcag ggttaccgtt ttccgctgac cttcggtggt   300
ggtaccaaag ttgaaatcaa acgtacggta gcggccccat ctgtcttcat cttcccgcca   360
tctgatgagc agttgaaatc tggaactgcc tctgttgtgt gcctgctgaa taacttctat   420

```
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 29
<211> LENGTH: 234
<212> TYPE: PRT
<213> ORGANISM: Artificial
<220> FEATURE:
<223> OTHER INFORMATION: Ab652 light chain (variable and constant) with
      signal sequence

<400> SEQUENCE: 29

```
Met Ser Val Pro Thr Gln Val Leu Gly Leu Leu Leu Leu Trp Leu Thr
1               5                   10                  15

Asp Ala Arg Cys Asp Ile Gln Met Thr Gln Ser Pro Ser Ser Leu Ser
            20                  25                  30

Ala Ser Val Gly Asp Arg Val Thr Ile Thr Cys Leu Ala Ser Glu Asp
        35                  40                  45

Ile Ser Asn Tyr Leu Ala Trp Tyr Gln Gln Lys Pro Gly Lys Ala Pro
    50                  55                  60

Lys Leu Leu Ile Tyr His Thr Ser Arg Leu Gln Asp Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Gly Tyr
            100                 105                 110

Arg Phe Pro Leu Thr Phe Gly Gly Gly Thr Lys Val Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 30
<211> LENGTH: 702
<212> TYPE: DNA
<213> ORGANISM: Artificial
<220> FEATURE:
<223> OTHER INFORMATION: Ab652 light chain (variable and constant) with
      signal sequence

<400> SEQUENCE: 30

```
atgtctgtcc ccacccaagt cctcggactc ctgctactct ggcttacaga tgccagatgc    60
gatatccaga tgacccagag tccaagcagt ctctccgcca gcgtaggcga tcgtgtgact    120
```

```
attacctgtc tggctagcga ggacatctcc aactacctgg cgtggtatca gcagaaaccg      180
ggtaaagcgc cgaaactgct gatctatcac acttcccgtc tgcaggacgg tgttccgtct      240
cgtttctctg gttccggttc tggtacggac ttcaccctga ccatctcttc tctgcagcca      300
gaagacttcg cgacttacta ctgccagcag ggttaccgtt ttccgctgac cttcggtggt      360
ggtaccaaag ttgaaatcaa acgtacggta gcggccccat ctgtcttcat cttcccgcca      420
tctgatgagc agttgaaatc tggaactgcc tctgttgtgt gcctgctgaa taacttctat      480
cccagagagg ccaaagtaca gtggaaggtg gataacgccc tccaatcggg taactcccag      540
gagagtgtca cagagcagga cagcaaggac agcacctaca gcctcagcag cacccctgacg     600 ctgagcaaag cagactacga gaaacacaaa gtctacgcct gcgaagtcac ccatcagggc      660
ctgagctcgc ccgtcacaaa gagcttcaac aggggagagt gt                        702
```

<210> SEQ ID NO 31
<211> LENGTH: 119
<212> TYPE: PRT
<213> ORGANISM: Artificial
<220> FEATURE:
<223> OTHER INFORMATION: Ab652 VH

<400> SEQUENCE: 31

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Tyr
            20                  25                  30

His Val Gln Trp Ile Arg Gln Pro Pro Gly Lys Ala Leu Glu Trp Leu
        35                  40                  45

Gly Val Met Trp Ser Asp Gly Asp Thr Ser Phe Asn Ser Val Leu Lys
    50                  55                  60

Ser Arg Leu Thr Ile Ser Arg Asp Thr Ser Lys Ser Gln Val Val Leu
65                  70                  75                  80

Thr Met Thr Asn Met Asp Pro Val Asp Thr Ala Thr Tyr Tyr Cys Ala
                85                  90                  95

Arg Asp Gly Thr Ile Ala Ala Met Asp Tyr Phe Asp Tyr Trp Gly Gln
            100                 105                 110

Gly Thr Leu Val Thr Val Ser
        115
```

<210> SEQ ID NO 32
<211> LENGTH: 357
<212> TYPE: DNA
<213> ORGANISM: Artificial
<220> FEATURE:
<223> OTHER INFORMATION: Ab652 VH

<400> SEQUENCE: 32

```
caggtgaccc tgaaagaatc tggtccggtt ctggtgaaac caacggaaac cctgactctg       60
acgtgcaccg tttctggttt ctctctgacc aactaccacg ttcagtggat cgtcagccg       120 ccgggtaaag cgctggaatg gctgggtgtt atgtggagcg acggtgacac cagcttcaac      180
tctgtgctga aatctcgcct gaccatctcc cgtgatactt ccaaatccca ggttgtgctg      240
accatgacga acatggaccc ggtagatact gcaacctact actgtgcacg tgatggcact      300
atcgcggcta tggattactt cgactattgg ggtcagggta ccctggttac cgtctcg        357
```

<210> SEQ ID NO 33

<211> LENGTH: 138
<212> TYPE: PRT
<213> ORGANISM: Artificial
<220> FEATURE:
<223> OTHER INFORMATION: Ab652 VH with signal sequence

<400> SEQUENCE: 33

```
Met Glu Trp Ser Trp Val Phe Leu Phe Phe Leu Ser Val Thr Thr Gly
1               5                   10                  15

Val His Ser Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
        35                  40                  45

Thr Asn Tyr His Val Gln Trp Ile Arg Gln Pro Pro Gly Lys Ala Leu
    50                  55                  60

Glu Trp Leu Gly Val Met Trp Ser Asp Gly Asp Thr Ser Phe Asn Ser
65                  70                  75                  80

Val Leu Lys Ser Arg Leu Thr Ile Ser Arg Asp Thr Ser Lys Ser Gln
                85                  90                  95

Val Val Leu Thr Met Thr Asn Met Asp Pro Val Asp Thr Ala Thr Tyr
            100                 105                 110

Tyr Cys Ala Arg Asp Gly Thr Ile Ala Ala Met Asp Tyr Phe Asp Tyr
        115                 120                 125

Trp Gly Gln Gly Thr Leu Val Thr Val Ser
    130                 135
```

<210> SEQ ID NO 34
<211> LENGTH: 414
<212> TYPE: DNA
<213> ORGANISM: Artificial
<220> FEATURE:
<223> OTHER INFORMATION: Ab 652 VH with signal sequence

<400> SEQUENCE: 34

```
atggaatgga gctgggtctt tctcttcttc ctgtcagtaa ctacaggagt ccattctcag    60
gtgaccctga agaatctggt ccggttctgt gtgaaaccaa cggaaaccct gactctgacg   120
tgcaccgttt ctggtttctc tctgaccaac taccacgttc agtggattcg tcagccgccg   180
ggtaaagcgc tggaatggct gggtgttatg tggagcgacg gtgacaccag cttcaactct   240
gtgctgaaat ctcgcctgac catctcccgt gatacttcca atcccaggt tgtgctgacc   300 atgacgaaca tggacccggt agatactgca acctactact gtgcacgtga tggcactatc   360
gcggctatgg attacttcga ctattggggt cagggtaccc tggttaccgt ctcg         414
```

<210> SEQ ID NO 35
<211> LENGTH: 223
<212> TYPE: PRT
<213> ORGANISM: Artificial
<220> FEATURE:
<223> OTHER INFORMATION: Ab652 heavy chain (variable and constant)

<400> SEQUENCE: 35

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Thr Asn Tyr
            20                  25                  30

His Val Gln Trp Ile Arg Gln Pro Pro Gly Lys Ala Leu Glu Trp Leu
        35                  40                  45

Gly Val Met Trp Ser Asp Gly Asp Thr Ser Phe Asn Ser Val Leu Lys
```

```
                50                  55                  60
Ser Arg Leu Thr Ile Ser Arg Asp Thr Ser Lys Ser Gln Val Val Leu
 65                  70                  75                  80

Thr Met Thr Asn Met Asp Pro Val Asp Thr Ala Thr Tyr Tyr Cys Ala
                 85                  90                  95

Arg Asp Gly Thr Ile Ala Ala Met Asp Tyr Phe Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys
    210                 215                 220

<210> SEQ ID NO 36
<211> LENGTH: 669
<212> TYPE: DNA
<213> ORGANISM: Artificial
<220> FEATURE:
<223> OTHER INFORMATION: Ab652 heavy chain (variable and constant)

<400> SEQUENCE: 36
caggtgaccc tgaaagaatc tggtccggtt ctggtgaaac caacggaaac cctgactctg      60
acgtgcaccg tttctggttt ctctctgacc aactaccacg ttcagtggat cgtcagccg     120 ccgggtaaag cgctggaatg gctgggtgtt atgtggagcg acggtgacac cagcttcaac    180
tctgtgctga atctcgcct gaccatctcc cgtgatactt ccaaatccca ggttgtgctg     240
accatgacga acatggaccc ggtagatact gcaacctact actgtgcacg tgatggcact    300
atcgcggcta tggattactt cgactattgg ggtcaggta ccctggttac cgtctcgagc     360
gcttctacaa agggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540
ggactctact ccctcagcag cgtggtgacc gtgccctcca gcagcttggg cacccagacc    600
tacatctgca acgtgaatca caagcccagc aacaccaagg tggacaagaa agttgagccc    660
aaatcttgt                                                            669

<210> SEQ ID NO 37
<211> LENGTH: 242
<212> TYPE: PRT
<213> ORGANISM: Artificial
<220> FEATURE:
<223> OTHER INFORMATION: Ab652 heavy chain (variable and constant) with
      signal sequence

<400> SEQUENCE: 37

Met Glu Trp Ser Trp Val Phe Leu Phe Phe Leu Ser Val Thr Thr Gly
1               5                  10                  15
```

-continued

```
Val His Ser Gln Val Thr Leu Lys Glu Ser Gly Pro Val Leu Val Lys
            20                  25                  30

Pro Thr Glu Thr Leu Thr Leu Thr Cys Thr Val Ser Gly Phe Ser Leu
            35                  40                  45

Thr Asn Tyr His Val Gln Trp Ile Arg Gln Pro Pro Gly Lys Ala Leu
 50                  55                  60

Glu Trp Leu Gly Val Met Trp Ser Asp Gly Asp Thr Ser Phe Asn Ser
 65                  70                  75                  80

Val Leu Lys Ser Arg Leu Thr Ile Ser Arg Asp Thr Ser Lys Ser Gln
                85                  90                  95

Val Val Leu Thr Met Thr Asn Met Asp Pro Val Asp Thr Ala Thr Tyr
            100                 105                 110

Tyr Cys Ala Arg Asp Gly Thr Ile Ala Ala Met Asp Tyr Phe Asp Tyr
            115                 120                 125

Trp Gly Gln Gly Thr Leu Val Thr Val Ser Ser Ala Ser Thr Lys Gly
130                 135                 140

Pro Ser Val Phe Pro Leu Ala Pro Ser Ser Lys Ser Thr Ser Gly Gly
145                 150                 155                 160

Thr Ala Ala Leu Gly Cys Leu Val Lys Asp Tyr Phe Pro Glu Pro Val
                165                 170                 175

Thr Val Ser Trp Asn Ser Gly Ala Leu Thr Ser Gly Val His Thr Phe
            180                 185                 190

Pro Ala Val Leu Gln Ser Ser Gly Leu Tyr Ser Leu Ser Ser Val Val
            195                 200                 205

Thr Val Pro Ser Ser Ser Leu Gly Thr Gln Thr Tyr Ile Cys Asn Val
            210                 215                 220

Asn His Lys Pro Ser Asn Thr Lys Val Asp Lys Lys Val Glu Pro Lys
225                 230                 235                 240

Ser Cys
```

<210> SEQ ID NO 38
<211> LENGTH: 726
<212> TYPE: DNA
<213> ORGANISM: Artificial
<220> FEATURE:
<223> OTHER INFORMATION: Ab652 heavy chain (variable and constant) with
      signal sequence

<400> SEQUENCE: 38

```
atggaatgga gctgggtctt tctcttcttc ctgtcagtaa ctacaggagt ccattctcag    60
gtgaccctga agaatctgg tccggttctg gtgaaaccaa cggaaaccct gactctgacg   120
tgcaccgttt ctggtttctc tctgaccaac taccacgttc agtggattcg tcagccgccg   180
ggtaaagcgc tggaatggct gggtgttatg tggagcgacg gtgacaccag cttcaactct   240
gtgctgaaat ctcgcctgac catctcccgt gatacttcca atcccaggt tgtgctgacc    300 atgacgaaca tggacccggt agatactgca acctactact gtgcacgtga tggcactatc   360
gcggctatgg attacttcga ctattggggt cagggtaccc tggttaccgt ctcgagcgct   420
tctacaaagg gcccatcggt cttccccctg gcaccctcct ccaagagcac ctctgggggc   480
acagcggccc tgggctgcct ggtcaaggac tacttccccg aaccggtgac ggtgtcgtgg   540
aactcaggcg ccctgaccag cggcgtgcac accttcccgg ctgtcctaca gtcctcagga   600
ctctactccc tcagcagcgt ggtgaccgtg ccctccagca gcttgggcac ccagacctac   660
atctgcaacg tgaatcacaa gcccagcaac accaaggtgg acaagaaagt tgagcccaaa   720
``` tcttgt                                                                    726

<210> SEQ ID NO 39
<211> LENGTH: 107
<212> TYPE: PRT
<213> ORGANISM: Artificial
<220> FEATURE:
<223> OTHER INFORMATION: Human VK1 2-1-(1) O2 JK4 acceptor framework

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 40
<211> LENGTH: 322
<212> TYPE: DNA
<213> ORGANISM: Artificial
<220> FEATURE:
<223> OTHER INFORMATION: Human VK1 2-1-(1) O2 JK4 acceptor framework

<400> SEQUENCE: 40
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctctcac tttcggcgga    300
gggaccaagg tggagatcaa ac                                              322

<210> SEQ ID NO 41
<211> LENGTH: 114
<212> TYPE: PRT
<213> ORGANISM: Artificial
<220> FEATURE:
<223> OTHER INFORMATION: Human VH2 3-1 2-26 JH4 acceptor framework

<400> SEQUENCE: 41

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val

```
             65                  70                  75                  80
Val Leu Thr Met Thr Asn Met Asp Pro Val Asp Thr Ala Thr Tyr Tyr
                    85                  90                  95
Cys Ala Arg Ile Tyr Phe Asp Tyr Trp Gly Gln Gly Thr Leu Val Thr
                100                 105                 110

Val Ser

<210> SEQ ID NO 42
<211> LENGTH: 342
<212> TYPE: DNA
<213> ORGANISM: Artificial
<220> FEATURE:
<223> OTHER INFORMATION: Human VH2 3-1 2-26 JH4 acceptor framework

<400> SEQUENCE: 42
caggtcacct tgaaggagtc tggtcctgtg ctggtgaaac ccacagagac cctcacgctg      60
acctgcaccg tctctgggtt ctcactcagc aatgctagaa tgggtgtgag ctggatccgt     120
cagcccccag ggaaggccct ggagtggctt gcacacattt tttcgaatga cgaaaaatcc     180
tacagcacat ctctgaagag caggctcacc atctccaagg acacctccaa aagccaggtg     240
gtccttacca tgaccaacat ggaccctgtg acacagccac atattactg tgcacggata     300 tactttgact actggggcca aggaaccctg gtcaccgtct cc                        342

<210> SEQ ID NO 43
<211> LENGTH: 14
<212> TYPE: PRT
<213> ORGANISM: Artificial
<220> FEATURE:
<223> OTHER INFORMATION: JH4

<400> SEQUENCE: 43

Tyr Phe Asp Tyr Trp Gly Gln Gly Thr Leu Val Thr Val Ser
1               5                   10

<210> SEQ ID NO 44
<211> LENGTH: 12
<212> TYPE: PRT
<213> ORGANISM: Artificial
<220> FEATURE:
<223> OTHER INFORMATION: JK4

<400> SEQUENCE: 44

Leu Thr Phe Gly Gly Gly Thr Lys Val Glu Ile Lys
1               5                   10

<210> SEQ ID NO 45
<211> LENGTH: 19
<212> TYPE: PRT
<213> ORGANISM: Artificial
<220> FEATURE:
<223> OTHER INFORMATION: Heavy chain signal peptide

<400> SEQUENCE: 45

Met Glu Trp Ser Trp Val Phe Leu Phe Phe Leu Ser Val Thr Thr Gly
1               5                   10                  15

Val His Ser

<210> SEQ ID NO 46
<211> LENGTH: 20
<212> TYPE: PRT
<213> ORGANISM: Artificial
<220> FEATURE:
```

```
<223> OTHER INFORMATION: Light chain signal peptide

<400> SEQUENCE: 46

Met Ser Val Pro Thr Gln Val Leu Gly Leu Leu Leu Leu Trp Leu Thr
1               5                   10                  15

Asp Ala Arg Cys
            20
```

The invention claimed is:

1. A method for treating a subject suffering from a pathological disorder mediated by interleukin-13 (IL-13), the method comprising administering to the subject by inhalation an effective amount of an anti-IL-13 antibody Fab or Fab' fragment comprising (i) a heavy chain variable domain comprising a CDR having the sequence given in SEQ ID NO:1 for CDR-H1, a CDR having the sequence given in SEQ ID NO:2 for CDR-H2 and a CDR having the sequence given in SEQ ID NO:3 for CDR-H3, and (ii) a light chain variable domain comprising a CDR having the sequence given in SEQ ID NO:4 for CDR-L1, a CDR having the sequence given in SEQ ID NO:5 for CDR-L2 and a CDR having the sequence given in SEQ ID NO:6 for CDR-L3.

2. The method according to claim 1 wherein the pathological disorder is selected from the group consisting of: asthmatic disorders, atopic disorders, chronic obstructive pulmonary disease (COPD), conditions involving airway inflammation, eosinophilia, fibrosis and excess mucus production, inflammatory conditions, autoimmune conditions, tumors or cancers and viral infection.

3. The method of claim 1, wherein the heavy chain variable domain comprises the sequence given in SEQ ID NO:31.

4. The method of claim 1, wherein the light chain variable domain comprises the sequence given in SEQ ID NO:23.

5. The method of claim 3, wherein the light chain variable domain comprises the sequence given in SEQ ID NO:23.

6. The method of claim 1, wherein the anti-IL-13 antibody fragment is a Fab' fragment comprising a heavy chain region comprising the sequence given in SEQ ID NO:31.

7. The method of claim 6, wherein the anti-IL-13 antibody fragment is a Fab' fragment comprising a light chain region comprising the sequence given in SEQ ID NO:25.

8. The method of claim 1, wherein the anti-IL-13 antibody fragment is a Fab' fragment comprising a light chain region comprising the sequence given in SEQ ID NO:25.

* * * * *